United States Patent
Long et al.

(10) Patent No.: US 10,593,007 B1
(45) Date of Patent: Mar. 17, 2020

(54) METHODS AND ARRANGEMENTS FOR CONFIGURING INDUSTRIAL INSPECTION SYSTEMS

(71) Applicant: Digimarc Corporation, Beaverton, OR (US)

(72) Inventors: Scott M. Long, Portland, OR (US); Christopher M. Haverkate, Newberg, OR (US)

(73) Assignee: Digimarc Corporation, Beaverton, OR (US)

( * ) Notice: Subject to any disclaimer, the term of this patent is extended or adjusted under 35 U.S.C. 154(b) by 0 days.

(21) Appl. No.: 15/816,098

(22) Filed: Nov. 17, 2017

Related U.S. Application Data

(63) Continuation-in-part of application No. 15/176,498, filed on Jun. 18, 2016, now Pat. No. 9,922,220.
(Continued)

(51) Int. Cl.
*G06T 1/00* (2006.01)
*G06K 9/62* (2006.01)
(Continued)

(52) U.S. Cl.
CPC .......... *G06T 1/0028* (2013.01); *G06K 9/6215* (2013.01); *G06T 5/40* (2013.01);
(Continued)

(58) Field of Classification Search
CPC ...... G06K 9/4671; G06K 9/6202; G06K 9/78; G06K 19/06037; G06K 7/10861; G06K 7/1456; G06K 9/6255; G06K 9/6267; G06K 9/00771; G06K 9/00765; G06K 9/00127; G06K 2209/19; G06K 9/00288; G06K 9/00577; G06K 9/00624; G06K 9/00664; G06K 9/3241; G06K 9/42; G06K 9/00335;
(Continued)

(56) References Cited

U.S. PATENT DOCUMENTS

| | | |
|---|---|---|
| 5,822,436 A | 10/1998 | Rhoads |
| 6,590,996 B1 | 7/2003 | Reed |

(Continued)

OTHER PUBLICATIONS

Feige, A threshold of In n for approximating set cover, Journal of the ACM, Jul. 1, 1998, pp. 634-652.
(Continued)

*Primary Examiner* — Aklilu K Woldemariam
(74) *Attorney, Agent, or Firm* — Digimarc Corporation

(57) ABSTRACT

In computer vision systems that need to decode machine-readable indicia from captured imagery, it is critical to select imaging parameters (e.g., exposure interval, exposure aperture, camera gain, intensity and duration of supplemental illumination) that best allow detection of subtle features from imagery. In illustrative embodiments, a Shannon entropy metric or a KL divergence metric is used to guide selection of an optimal set of imaging parameters. In accordance with other aspects of the technology, different strategies identify which spatial locations within captured imagery should be successively examined for machine readable indicia, in order to have a greatest likelihood of success, within a smallest interval of time. A great variety of other features and arrangements are also detailed.

29 Claims, 17 Drawing Sheets

Related U.S. Application Data

(60) Provisional application No. 62/547,033, filed on Aug. 17, 2017, provisional application No. 62/433,916, filed on Dec. 14, 2016, provisional application No. 62/424,183, filed on Nov. 18, 2016, provisional application No. 62/174,454, filed on Jun. 11, 2015.

(51) Int. Cl.
*H04N 19/91* (2014.01)
*G06T 5/40* (2006.01)
*H04N 19/44* (2014.01)

(52) U.S. Cl.
CPC ............ *H04N 19/44* (2014.11); *H04N 19/91* (2014.11); *G06T 2201/0052* (2013.01)

(58) Field of Classification Search
CPC .. G06K 9/00355; G06K 9/6268; G06K 3/012; G06K 3/0346; G06T 17/00; G06T 2207/10016; G06T 5/006; G06T 7/285; G06T 7/593; G06T 7/73; G06T 7/001; G06T 2207/20081; G06T 7/20; G06T 7/00; G06T 7/66; G06T 7/80; G06T 3/0056; G06T 1/0028; G06T 1/0021; G06T 2200/24; G06T 5/009; H04N 1/32251; H04N 1/00005; H04N 2201/3205; H04N 21/4394; H04N 21/44218; H04N 21/8106; H04N 2201/3225; H04N 5/23219; H04N 7/012; H04N 7/0137; H04N 13/128; H04N 1/00037; H04N 1/203; H04N 1/3224; H04N 21/23892; H04N 2201/3226; H04N 2201/3252; H04N 2201/3253; G06F 16/583; G06F 3/012; G06F 16/7837; G06F 16/50; A63F 13/42; A63F 13/428; G01C 21/00; B22F 2207/01; A61N 5/1048; G01N 27/44782; G01N 15/1475; G01R 21/133; G01R 35/00; H04Q 9/00; Y02B 90/241; Y04S 20/36; Y04S 20/525; Y04S 40/128; A61B 2090/367; A61B 6/5229; A61B 8/4245; G03B 13/00
USPC ....... 382/103, 128, 199, 164, 162, 296, 300, 382/345; 348/261, 448, 589

See application file for complete search history.

(56) References Cited

U.S. PATENT DOCUMENTS

| | | | |
|---|---|---|---|
| 6,674,919 B1* | 1/2004 | Ma | G06K 7/14 382/199 |
| 6,707,937 B1* | 3/2004 | Sobel | G06T 3/4007 345/589 |
| 6,952,485 B1 | 10/2005 | Davidson | |
| 7,013,021 B2 | 3/2006 | Sharma | |
| 7,548,663 B2* | 6/2009 | Chao | G06T 3/4007 348/448 |
| 7,672,474 B2 | 3/2010 | Nakamura | |
| 7,689,054 B1* | 3/2010 | Repperger | G06K 9/3241 382/162 |
| 8,290,308 B2* | 10/2012 | Nakagata | G06T 3/0056 348/448 |
| 8,745,541 B2* | 6/2014 | Wilson | G06F 3/017 715/863 |
| 8,903,130 B1* | 12/2014 | Carceroni | G06K 9/00765 382/103 |
| 8,913,103 B1* | 12/2014 | Sargin | G06K 9/00221 348/14.12 |
| 9,118,771 B2* | 8/2015 | Rodriguez | G01C 21/20 |
| 9,189,673 B2 | 11/2015 | Decoux | |
| 9,542,594 B2* | 1/2017 | Umeda | G06K 9/00228 |
| 9,602,783 B2* | 3/2017 | Sugishita | H04N 7/181 |
| 9,635,378 B2 | 4/2017 | Holub | |
| 9,747,656 B2 | 8/2017 | Stach | |
| 2002/0042676 A1* | 4/2002 | Furusho | G05D 1/0246 701/300 |
| 2002/0057362 A1* | 5/2002 | Wredenhagen | H04N 5/142 348/441 |
| 2002/0153422 A1* | 10/2002 | Tsikos | G06K 7/10742 235/454 |
| 2004/0022444 A1* | 2/2004 | Rhoads | G06K 9/00577 382/232 |
| 2004/0170323 A1* | 9/2004 | Cootes | G06K 9/00275 382/199 |
| 2005/0041835 A1* | 2/2005 | Reed | G06T 1/0042 382/100 |
| 2005/0061878 A1* | 3/2005 | Barenburg | G06K 7/1434 235/385 |
| 2005/0175180 A1 | 8/2005 | Venkatesan | |
| 2005/0286802 A1* | 12/2005 | Clark | H04N 5/232 382/286 |
| 2006/0067593 A1* | 3/2006 | Erol | H04N 1/00283 382/309 |
| 2006/0070006 A1* | 3/2006 | Erol | H04N 1/00326 715/764 |
| 2006/0072165 A1* | 4/2006 | Erol | H04N 1/00326 358/426.12 |
| 2006/0173630 A1* | 8/2006 | Sipe | G06K 9/00127 702/19 |
| 2007/0257934 A1* | 11/2007 | Doermann | G06K 9/36 345/606 |
| 2008/0240019 A1 | 10/2008 | Bejerano | |
| 2009/0245579 A1* | 10/2009 | Hu | G03B 13/00 382/103 |
| 2009/0252419 A1* | 10/2009 | Knee | G06K 9/4609 382/199 |
| 2010/0054606 A1* | 3/2010 | Mishima | G06T 7/13 382/199 |
| 2010/0092037 A1* | 4/2010 | Peleg | G11B 27/034 382/103 |
| 2010/0103463 A1* | 4/2010 | Joshi | H04N 1/00326 358/1.16 |
| 2010/0135544 A1* | 6/2010 | Mattiuzzi | G06T 7/33 382/128 |
| 2010/0150434 A1 | 6/2010 | Reed | |
| 2011/0161076 A1* | 6/2011 | Davis | G06F 3/04842 704/231 |
| 2011/0211517 A1 | 9/2011 | Moscibroda | |
| 2012/0033875 A1* | 2/2012 | Bergman | G06T 7/11 382/164 |
| 2012/0078989 A1 | 3/2012 | Sharma | |
| 2012/0114170 A1* | 5/2012 | Simske | G06K 9/00577 382/100 |
| 2012/0284069 A1* | 11/2012 | Kemp | G06Q 30/0282 705/7.11 |
| 2013/0019216 A1 | 1/2013 | Vasudevan | |
| 2013/0061184 A1* | 3/2013 | Guo | G03F 1/70 716/52 |
| 2013/0223673 A1 | 8/2013 | Davis | |
| 2013/0278425 A1* | 10/2013 | Cunningham | G08B 13/246 340/572.1 |
| 2013/0325401 A1* | 12/2013 | Bouchard | G06F 17/11 702/181 |
| 2014/0052555 A1 | 2/2014 | MacIntosh | |
| 2014/0063197 A1* | 3/2014 | Yamamoto | G08G 1/166 348/46 |
| 2014/0112524 A1 | 4/2014 | Bai | |
| 2014/0119593 A1 | 5/2014 | Filler | |
| 2015/0016712 A1 | 1/2015 | Rhoads | |
| 2015/0127337 A1* | 5/2015 | Heigold | G10L 15/063 704/232 |
| 2015/0306505 A1* | 10/2015 | Vock | A43B 3/0005 463/42 |
| 2015/0317037 A1* | 11/2015 | Suzuki | G06F 3/0426 345/175 |

(56) References Cited

U.S. PATENT DOCUMENTS

| | | | |
|---|---|---|---|
| 2015/0325013 A1* | 11/2015 | Patnaik | G06T 7/11 |
| | | | 345/424 |
| 2015/0363670 A1* | 12/2015 | Sugishita | H04N 7/181 |
| | | | 382/155 |
| 2016/0321809 A1* | 11/2016 | Chukka | G06K 9/0014 |
| 2016/0360231 A1* | 12/2016 | Yuan | H04N 19/85 |
| 2017/0142340 A1* | 5/2017 | Kishi | H04N 5/23293 |

OTHER PUBLICATIONS

Set Cover article from Wikipedia archive, dated Jun. 3, 2015.
Stern, Set Cover Problem, Seminar in Theoretical Computer Science, MIT, Feb. 9, 2006.
Japanese patent document JP2005026797, with machine translation.

* cited by examiner

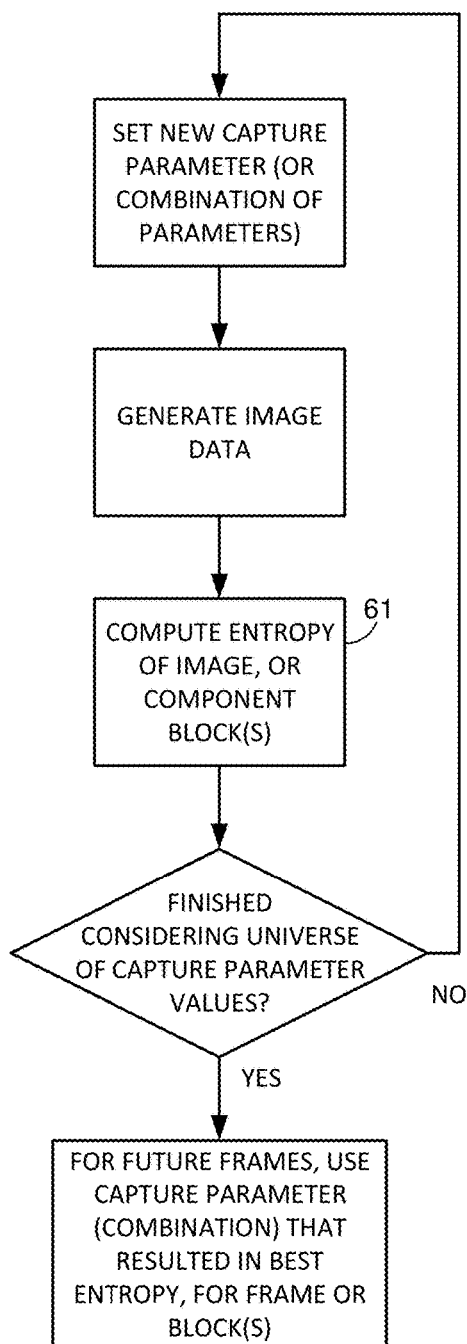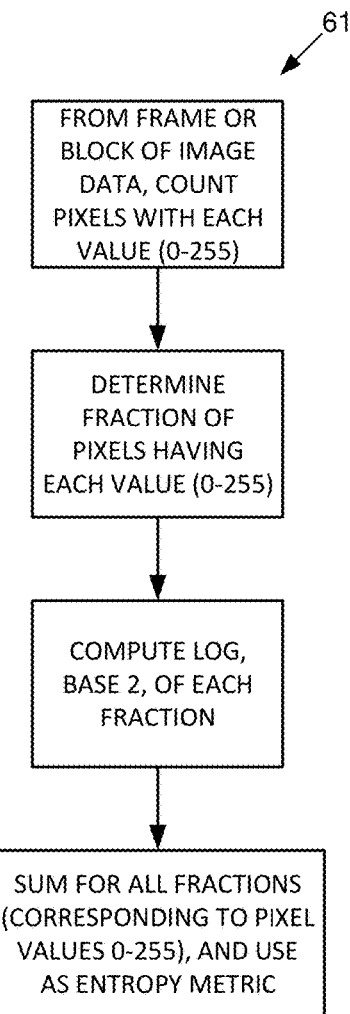
FIG. 6
FIG. 7

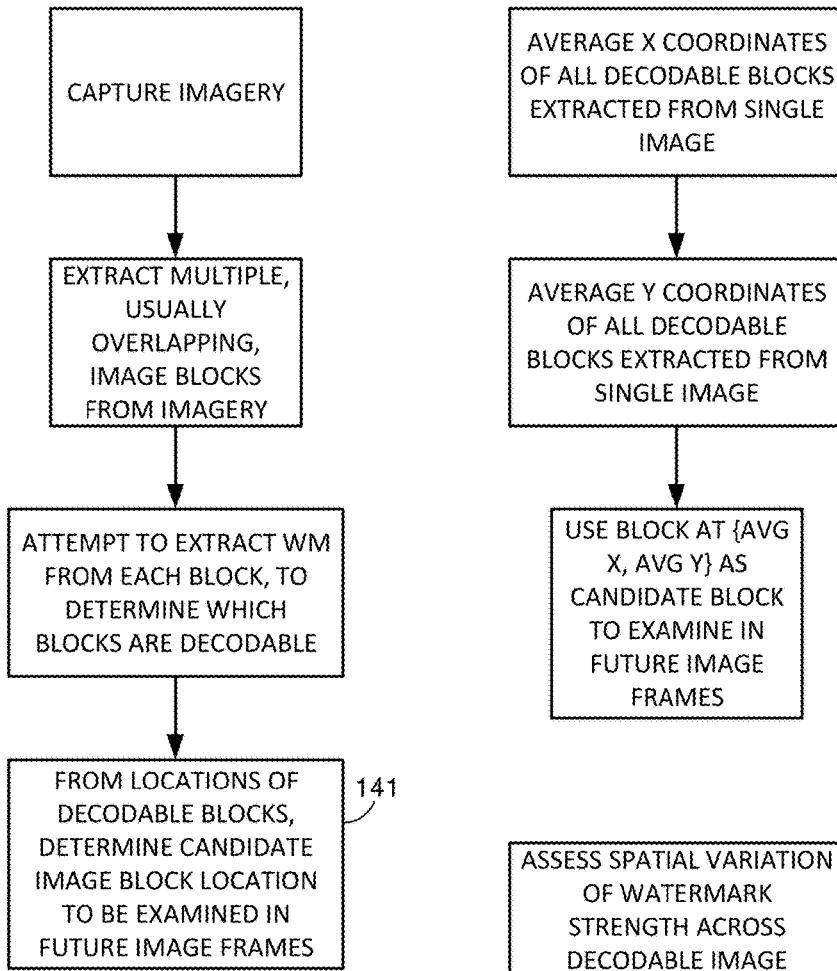
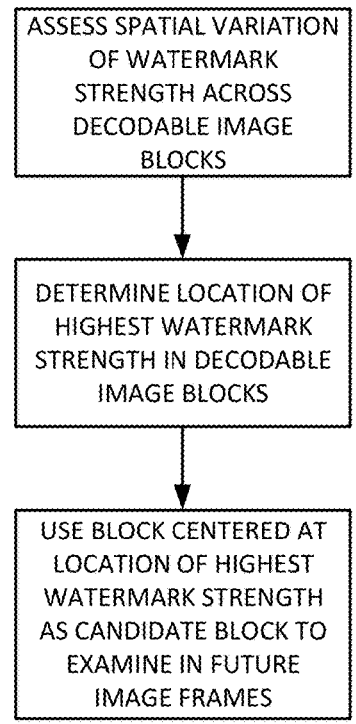
FIG. 14
FIG. 15
FIG. 16

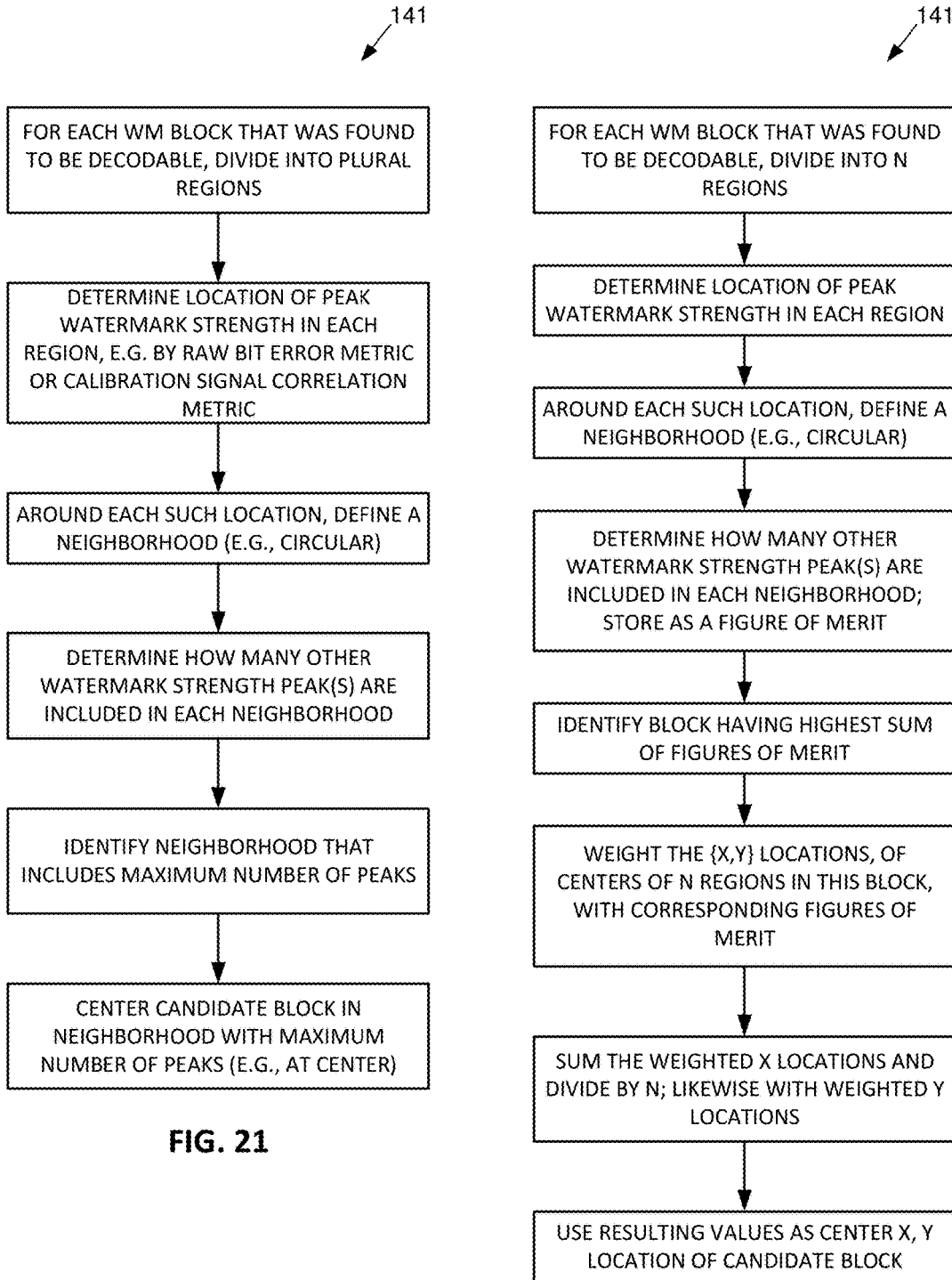

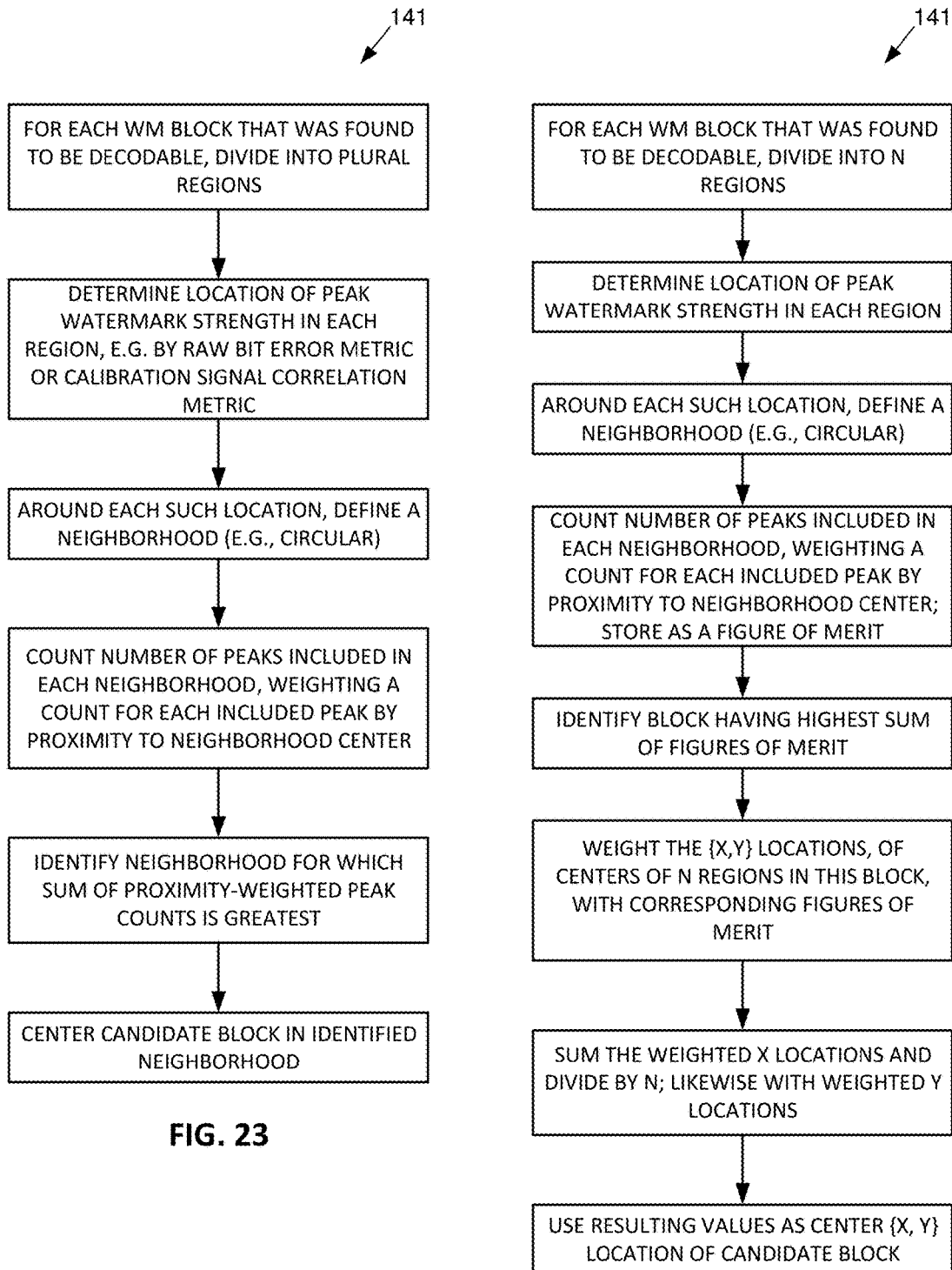

METHODS AND ARRANGEMENTS FOR CONFIGURING INDUSTRIAL INSPECTION SYSTEMS

RELATED APPLICATION DATA

This application claims priority to provisional applications 62/547,033, filed Aug. 17, 2017, 62/433,916, filed Dec. 14, 2016, and 62/424,183, filed Nov. 18, 2016. This application is also a continuation-in-part of allowed application Ser. No. 15/176,498, filed Jun. 8, 2016 (published as 20160364623), which claims priority to provisional application 62/174,454, filed Jun. 11, 2015. The disclosures of these applications are incorporated herein by reference.

BACKGROUND AND SUMMARY

Camera-based inspection systems are widely used to monitor operation of industrial processes. One example is in the food industry, where cameras are positioned at different locations along a production line that packages food, or that applies labels to food containers. Computer vision systems monitor the imagery collected by such systems to assure that the production process is proceeding as expected, without aberration or incident.

One of the functions performed by such industrial vision system is to sense and decode machine-readable markings to assure that correct components are being used. Again taking the food industry as an example, when assembling multi-part packaging, it is critical that lidded containers be topped with lids that correctly correspond to the container. For instance, if a container is correctly marked as containing chocolate-peanut ice cream, but is incorrectly capped with a lid indicating chocolate ice cream, serious consequences may result.

Similarly, many products include multiple labels. A bottle of catsup, for example, commonly includes a front label, a back label, and a neck label. Again, it is essential that such labels be applied in correct groupings.

Small barcode-like markings, termed Datamatrix codes, sometimes are included on packaging components and used to check that packaging components or labels are correctly used together. But these markings detract from the aesthetics of packaging. More recently, as detailed in Applicant's patent publication 20160267620, steganographic digital watermarks have been employed for such purpose.

As is familiar, a steganographic digital watermark comprises a subtle printed marking, e.g., included in packaging artwork, that conveys a plural-bit data payload in essentially invisible form. The presence of such marking is not generally apparent to an untrained consumer, who inspects a digitally watermarked package from a typical reading distance of 20 inches, in normal retail lighting (e.g., 75 to 100 foot-candles), and who has not previously been alerted to the watermark's existence. Yet, when a camera captures imagery of such a watermarked package, and the imagery is analyzed by corresponding watermark decoding software, the subtle markings can be discerned, and decoded to recover the plural-bit payload.

Due to the subtle nature of the markings, it is particularly important that imagery be captured using the best possible camera parameters for that environment (e.g., exposure interval, gain, aperture, etc.). Due to the inherent complexity of industrial production lines, and the myriad steps needed to prepare such lines for operation, it is desirable that the set-up of the companion inspection systems be as simple and quick as possible, so as to avoid compounding the complexity and set-up delays. Once the line is running, the inspection system must be reliable, so that the production line needn't be stopped to correct a problem with an imaging parameter or decoding operation.

In one aspect, the present technology involves varying camera capture parameters while the system repeatedly collects image data from one or more samples. An exemplary sample is a calibration target, printed with a grayscale gradient that ranges linearly from black to white. For each different set of camera capture parameters, the values of collected pixel data are compiled in a histogram, indicating a number of pixels counted with each respective level of gray (e.g., 0-255). An entropy metric is computed for each of the histograms. The set of capture parameters that yields the histogram with the highest entropy measurement is thereafter used to collect imagery from products, e.g., on a food packaging line, for watermark analysis. By so-doing, methods according to this aspect of the present technology guide selection of an optimal set of imaging parameters, to best allow machine detection of subtle features from imagery.

A camera used in such an inspection system might produce an image frame of 1280×960 pixels, yet a watermarked label or lid may occupy only a fraction of this area. Given the high speeds at which such inspection systems may operate, it is helpful for the decoder to know—in advance—in what parts of the captured image frame the watermark is likely to be found, so that the watermark decoder can concentrate its decoding efforts on such regions and extract the watermark payload before the next image is ready for processing.

Thus, a further aspect of the present technology involves analyzing reference imagery gathered by the inspection camera, to determine which parts of the image frame offer the highest probabilities of containing decodable watermark data.

The foregoing and other features and advantages of the technology will be more readily apparent from the following detailed description, which proceeds with reference to the accompanying drawings.

BRIEF DESCRIPTION OF THE DRAWINGS

FIG. 6 is a flow chart detailing an algorithm according to one aspect of the present technology.

FIG. 7 is a flow chart detailing a sub-algorithm that optionally can be used with the algorithm of FIG. 6.

FIG. 14 is a flow chart detailing an algorithm according to another aspect of the present technology.

FIGS. 15-24 are flow charts detailing algorithms that optionally can be used with the algorithm of FIG. 14.

DETAILED DESCRIPTION

Due to the subtle nature of digital watermark signals, it is important that images submitted for watermark decoding be captured under the best possible conditions. If the image depiction of the watermark is even slightly underexposed or overexposed, or if the camera gain is set too high or too low, watermark decoding suffers.

A further complication is camera non-linearity. The sensors in many industrial inspection camera systems are relatively inexpensive, and their accuracy suffers. Ideally, when a camera sensor is shielded from all illumination, each of its pixels should produce an output signal of zero. Similarly, when a camera sensor is exposed to the maximum level of luminance for which it is designed, each of its pixels should produce the highest possible output state (e.g., 255, in an 8-bit sensor).

Moreover, when the luminance presented to a camera sensor increases by a given percentage (e.g., 100%), the output signal from each of its pixels should increase by the same percentage (subject to quantization effects).

Figure 1:
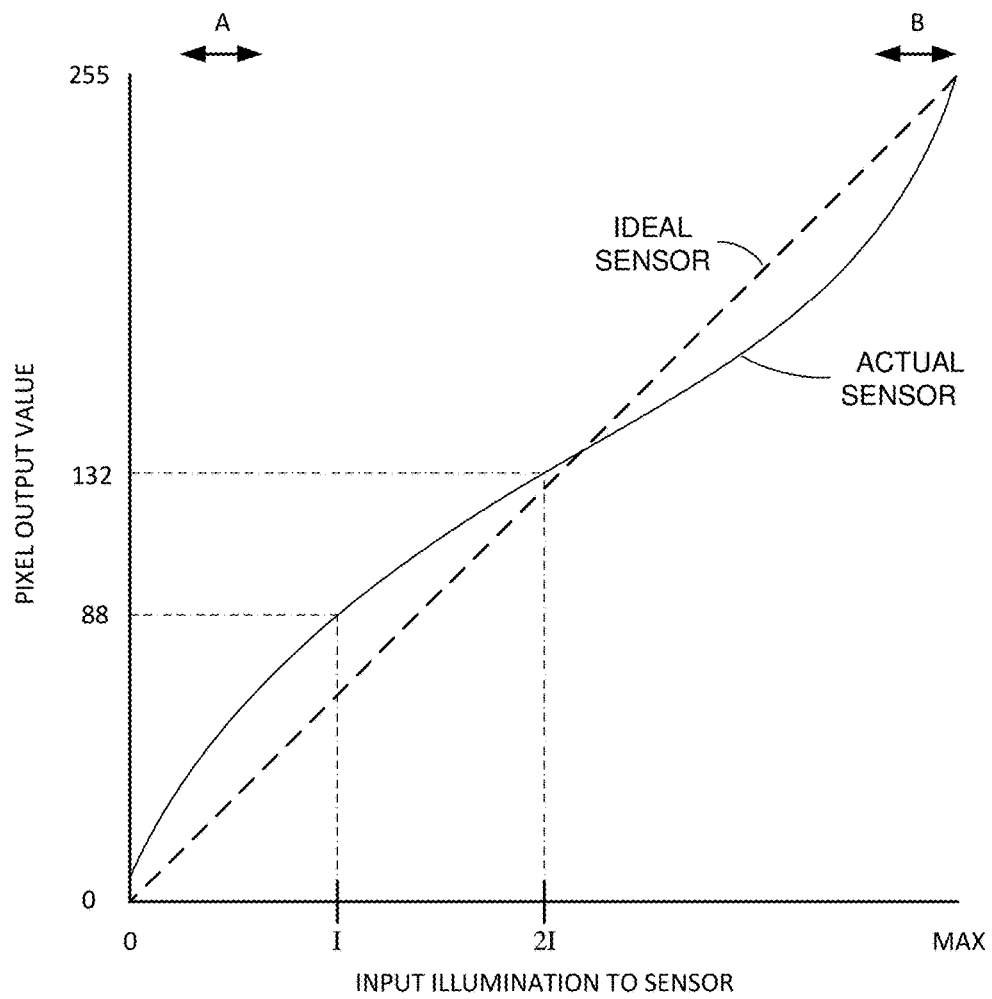
FIG. 1 is a plot illustrating how a pixel output signal may non-linearly as a function of incident illumination.

No camera sensor meets these ideals, and some sensors are radically at variance. FIG. 1 shows one sample pixel response curve, detailing how its output signal varies non-linearly with input illumination. For one level of incident illumination, "I," the pixel produces an output signal of 88. If the level of incident illumination is doubled, to "2I," the pixel output signal is not doubled, to 176. Instead, the pixel output signal is 132.

In most industrial inspection applications, such sensing errors are of little consequence. However, in the context of watermark decoding, they can be critical.

To make the best out of such a situation, Applicant has found it advantageous to probe a sensor's responses across a variety of different imaging parameters, such as exposure interval, exposure (lens) aperture, and camera gain. (Camera gain may be thought of as changing the level of incident illumination that yields a full scale output signal, such as 255.)

Some sets of parameters will lead to over-exposure of the imagery, washing out image highlights. Some sets of parameters will lead to under-exposure, losing detail in the resulting shadows.

A watermark signal typically spans just a narrow range of luminance variations for a given item of product artwork. For example, if a watermark appears in a dark region of product label artwork, e.g., comprising darker blue markings within a flood of dark blue ink, the watermark variation may span a subset of the range "A" in FIG. 1. Conversely, if a watermark appears in a light region of product label artwork, e.g., comprising subtle yellow markings on a white background, the watermark variation may span a subset of the range "B" in FIG. 1. If the gain of the camera is too low, then both such watermark variations are represented by unduly small variations in pixel output values. If the gain of the camera is too high, then watermark variations up in the "B" range of FIG. 1 may be lost, as the gain causes all such incident light levels to produce an output signal of 255.

Figure 2:
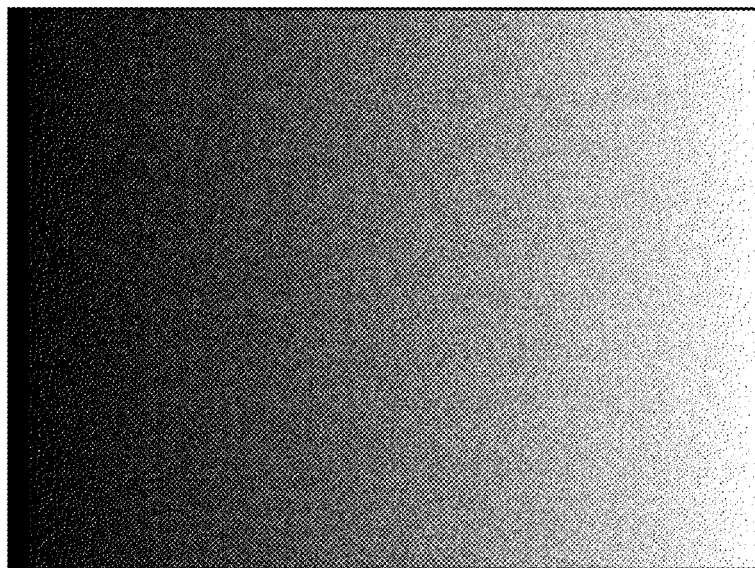
FIG. 2 shows a linear gradient printed target.

One way to probe the camera's responses across a variety of different imaging parameters is to put a greyscale gradient target (e.g., as shown in FIG. 2) on the production line, at the location where a watermarked product will normally appear, and capture multiple images of it. Each image is captured with a different combination of imaging parameters. Multiple values for each parameter can be established, e.g., by sampling linearly or otherwise across the parameter's possible range, to yield 10, 20, or more, different values. Each such value is then tried in combination with each possible combination of the other imaging parameter(s).

If just two parameters are probed (e.g., camera gain and lens aperture), and ten values are tried for each, then 100 images of the target are captured. If three parameters are probed (e.g., camera gain, lens aperture and exposure interval), and 20 different values are tried for each, then 8000 images of the target are captured.

If an ideal camera, having a sensor size of 1280×960 pixels (i.e., 1,228,00 pixels in all) imaged the linear gradient target of FIG. 2, and the target perfectly filled the imaging frame, then $11256^{th}$ of the pixels should produce an output signal of 0, $11256^{th}$ of the pixels should produce an output signal of 1, and so on up to an output signal of 255. That is, there should be 4800 pixels with an output signal of 0, 4800 pixels with an output signal of 1, etc.

Such a set of pixel statistics can be regarded as a histogram—defining a count of pixels for each possible output signal.

In actual practice, of course, no image of the FIG. 2 target—regardless of imaging parameters—yields a histogram with a count of 4800 for each of the 256 different pixel output values. But some are much worse (and better) than others.

Figures 3, 4:
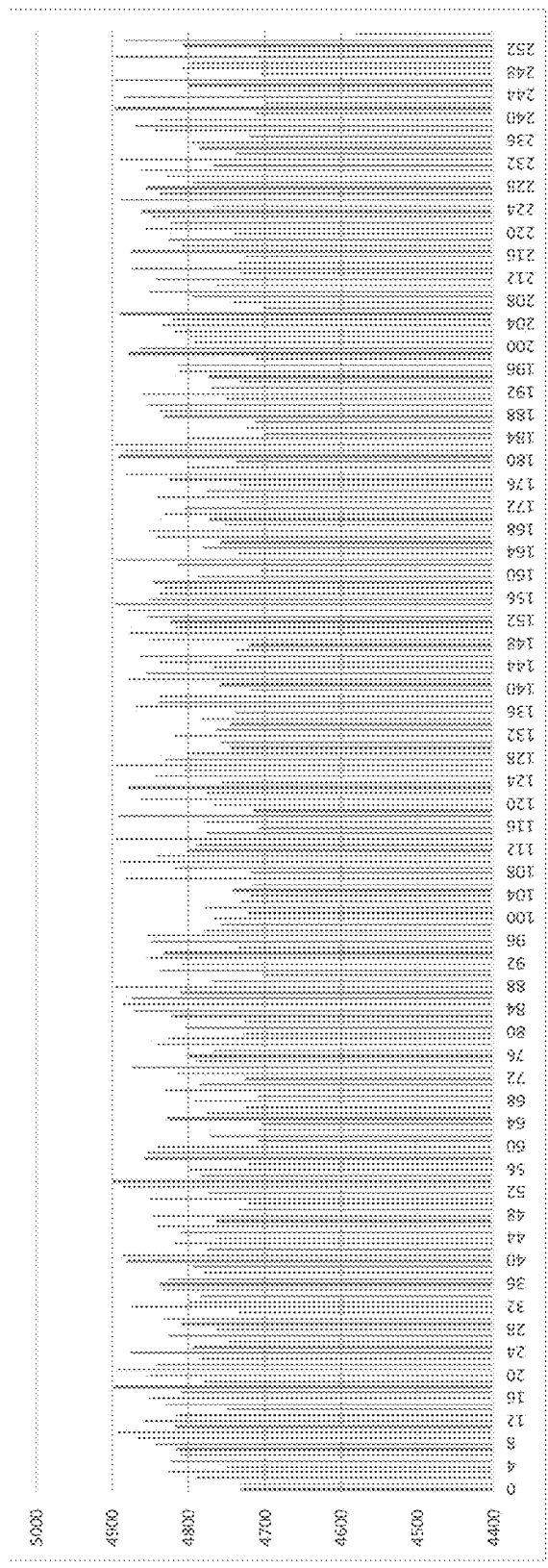
FIG. 3 is a histogram showing the number of pixels of value 0, 1, 2, . . . 255, captured from the target of FIG. 2, using a particular set of imaging parameters.
FIG. 4 illustrates how an entropy metric varies with histogram entropy.

FIG. 3 shows an illustrative histogram of a nearly-ideal imaging sensor. Although there are variations among the count of the different histogram "bins," the counts are generally consistent.

In contrast, if the lens aperture were too small, or if the exposure interval were too short, the low-valued pixels would predominate, yielding a histogram with higher bin counts on the left. (A similar effect would be observed if the gain is set too low.) Conversely, if the lens aperture were too large, or the exposure interval were too large, the high-valued pixels would predominate, yielding a histogram with higher bin counts on the right. (A similar effect would be observed if the gain is set too high.)

To quantify a figure of merit of different histograms (produced by imaging a gradient target with different imaging parameters), a particular embodiment of the present technology employs the Shannon entropy metric. Although well known in information theory and in other applications, the Shannon metric has not—to Applicant's knowledge—been previously utilized as a criterion by which imaging parameters in a watermark decoding system may be evaluated.

Briefly, this Shannon metric is the sum, across each bin of a histogram, of the fraction of image pixels in that bin, times the log (base2) of that fraction:

$$H = \sum_{i=0}^{n} -(P_i) * \log 2(P_i)$$

where n is the number of possible pixel values, and $P_i$ is the fraction of image pixels that have the value i.

In the present example, with 1,228,800 pixels in the image, this may be expressed as:

$$H = \sum_{i=0}^{255} -(L_i/1,228,800) * \log2(L_i/1,228,800)$$

where $L_i$ is the count of pixels in the image having the value i.

This may be made clearer by the examples shown in the tables of FIG. 4. On the left of the figure, at columns "A," is an excerpt of a histogram, showing idealized pixel counts of 4800 for each of bins 0, 1, 2, 3, 4, 5, . . . 255. The fraction of pixels in each bin is thus 4800/1,228,800, or 0.00390625. The log (base2) of this value is −8. The product of the fraction, and the log, is 0.03125. Summed across all 256 bins yields a final Shannon metric H of 8.0

The middle of FIG. 4, at columns "B," shows a slightly more chaotic distribution of pixel values (corresponding to the histogram of FIG. 3). Here the Shannon metric is slightly under 8.0, i.e., 7.99987.

The right of FIG. 4, at columns "C" shows a still more chaotic distribution of pixel values. Here the Shannon metric is still lower, i.e., 7.9885.

In accordance with this aspect of Applicant's technology, such a metric is computed for each of the dozens, or hundreds, or thousands, of test images, captured depicting the test target using different imaging parameters. The set of parameters that yields the highest metric is used thereafter when the industrial line is running in production mode— capturing imagery from each item as it goes by (commonly triggered by break-beam item detection logic), and analyzing the resulting images for watermarked identifiers.

Figure 5:
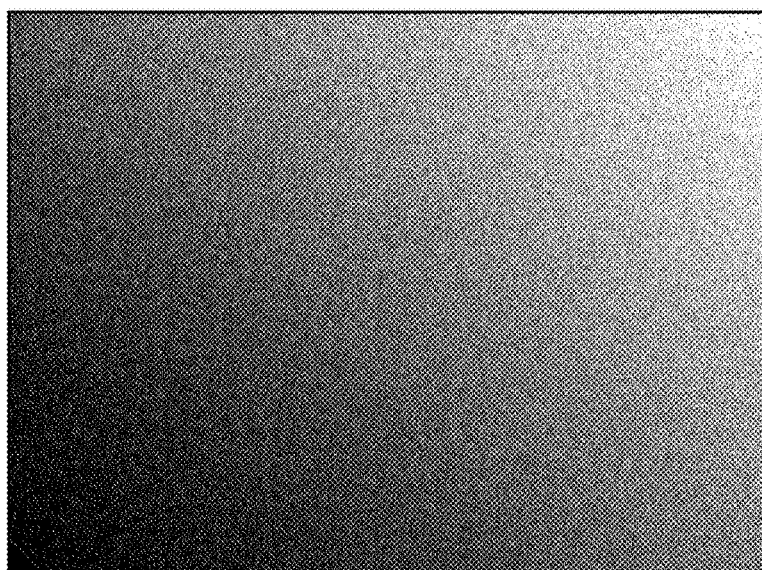
FIG. 5 is a variant of the FIG. 2 printed target.

It is not essential that a greyscale test target, which varies linearly from absolute white to absolute black, with equal area devoted to each different greyscale value, be utilized. In other arrangements, different types of targets can be employed, as may serve different applications. FIG. 5 shows one slight variation—a gradient target that varies from corner to opposite corner, instead of side to opposite side. This has the effect of reducing the count of pixels having low and high values, and increasing the count of pixels at mid-grey values. In the foregoing equation, the value of $P_i$ will be expected to have different values for different bins. Some other options include targets that are not grey-scaled but of color, targets that don't extend all the way to absolute black (or absolute white), gradients that vary non-linearly, etc.

Typically, the entropy metric is a concave function, with a single local maximum that is revealed as the imaging parameters (exposure interval, lens aperture, camera gain) are changed. In a particular embodiment, the search for optimum parameters can be roughly halved by varying each of the parameters from one extreme towards the other, and not continuing such variation once the metric has reached a maximum and starts decreasing in value. In a particular embodiment, it was found best to start with maximum exposure and maximum camera gain, and reduce these parameters until the entropy metric starts diminishing in value.

In some embodiments, the imagery of the gradient pattern collected during the testing phase is low-pass filtered prior to analysis, to reduce noise effects. A blurring kernel, such as a Gaussian blur kernel of size 3×3 or 5×5 pixels, can be used.

Another approach to noise reduction in the imagery captured for analysis is to average corresponding pixels across several (e.g., ten) frames captured with each different set of imaging parameters. The resulting average pixel values are collected in a single frame, and analyzed as above to determine an entropy metric corresponding to each different set of imaging parameters.

In an alternative embodiment, an entropy metric is not computed based on the entirety of a captured frame. Instead, multiple metrics are computed—each from a different region (e.g., pixel block) within the frame. For example, an image frame can be divided into an array of 4×3 or 10×10 blocks, and an entropy metric can be computed for each such block. Different blocks may thereby be found to be optimally-imaged with different sets of parameters. That is, the best entropy metric may be achieved by different combinations of imaging parameters at different locations in the frame. In subsequent use, if a watermark or other indicia of interest is repeatedly found to be located at a particular position within a frame, then the analyzed block that most nearly spatially corresponds to that position can be identified, and the imaging parameters that yielded the highest entropy metric for that block can be used in subsequent image captures.

In other arrangements, a gradient test pattern is not employed. Instead, the imaging parameters are established based on runs of the production line involving actual packages. In particular, images of the packages are captured under different combinations of imaging parameters, as described above in connection with gradient targets, and entropy metrics are computed. After such data collection and analysis, the parameters that are found to yield the maximum metric are selected for further, ongoing operation of the production line.

Figure 8:
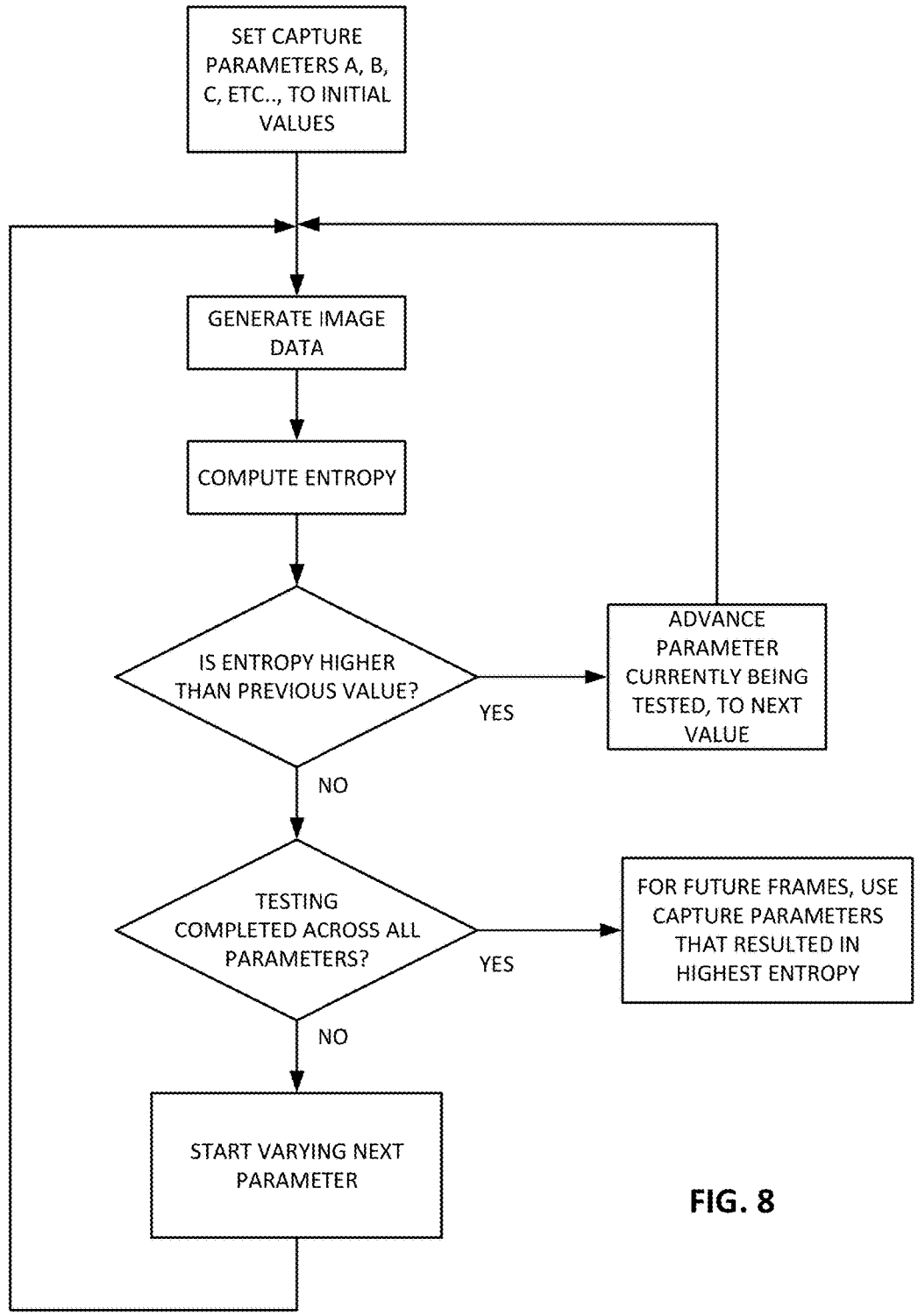
FIG. 8 is a flow chart detailing an algorithm according to another aspect of the present technology FIG. 9 helps illustrate an analysis of an image frame for decodable digital watermark blocks.

FIGS. 6-8 are flowcharts expressing aspects and variations of the algorithms detailed above. FIG. 7, for example, details a representative sub-algorithm that can be used to compute entropy in block 61 of FIG. 6. Such algorithms can be implemented in various forms, e.g., in software executing on conventional computer system hardware, or in custom hardware, etc., as further detailed below. ("WM" is used in certain of the figures as an abbreviation for "watermark.")

Diversity Block Selection for Watermark Decoding

Once a well-exposed image has been captured, the task becomes to locate and read a watermark indicia depicted somewhere in the image, quickly, before the next-captured image is presented for analysis. (In many applications, when an object on the production line breaks an LED/photosensor path, a burst of 3-10 images are captured, e.g., at a rate of 20-100 per second).

In an exemplary system, the watermark payload is formatted into a binary sequence, which is encoded and mapped to the locations of a tile. For illustration, we describe an implementation of an I by J array of bit cells. The parameters, I and J are integers, and the tile is comprised of an I by I array of bit cells. The size of the tile is configurable and depends on application requirements, such as payload capacity per unit area, robustness, and visibility. Payload capacity increases per unit area with the increase in bit cells per unit area. This additional capacity may be used to improve robustness by redundantly encoding the payload in plural bit cells. Visibility tends to decrease with higher spatial resolution (higher CPI), as the HVS is less sensitive to changes at higher spatial frequencies. Examples of bit cell array sizes include 64 by 64, 128 by 128, 256 by 256 and 512 by 512. While each of these is square and has a dimension that is power of 2, the tile need not be so limited. The bit cells correspond to spatial locations within a tile. In particular, the spatial locations correspond to pixel samples at a configurable spatial resolution, such as 75-600 DPI. The payload is repeated in contiguous tiles of artwork. An instance of the payload is encoded in each tile, occupying a block of artwork having a size that depends on the number of bit cells per tile and the spatial resolution. The tile is redundantly encoded in several contiguous tiles, providing added robustness, as the detector accumulates signal estimates for a payload across tiles. Additionally, the entire payload may be extracted from a portion of a tile in configurations where it is redundantly encoded in sub-tile regions.

A few examples will help illustrate the parameters of a tile. The spatial resolution of the bit cells in a tile may be expressed in terms of cells per inch (CPI). This notation provides a convenient way to relate the bit cells spatially to pixels in an image, which are typically expressed in terms of dots per inch (DPI). Take for example a bit cell resolution of 75 CPI. When a tile is encoded into an image with a pixel resolution of 300 DPI, each bit cell corresponds to a 4 by 4 array of pixels in the 300 DPI image. As another example, each bit cell at 150 CPI corresponds to a region of 2 by 2 pixels within a 300 DPI image, or a region of 4 by 4 pixels within a 600 DPI image. Now, considering tile size in terms of I by J bit cells and setting the size of a bit cell, we can express the tile size by multiplying the bit cell dimension by the number of bit cells per horizontal and vertical dimension of the tile. A tile with 128 by 128 bit cells is about 1.7 by 1.7 inches at a CPI of 75 and about 0.85 by 0.85 inches at a CPI of 150. Each provides the same number of embedding locations per tile (16,384), but occupies a different spatial area based on the spatial resolution the two-dimensional array of bit cells. At each of these 16,384 tiny regions, the luminance of the artwork is subtly increased or decreased to thereby encode a plural bit (e.g., 64-bit) payload.

One particular method of encoding a plural-bit watermark payload in imagery of host artwork begins by error-correction coding the payload to yield a large set of raw bits. (Techniques such as block codes, BCH, Reed Solomon, convolutional codes, and turbo codes may be used.) These raw bits are XORed with a pseudo-random noise sequence. Each result is spatially mapped to plural of the 16,384 different regions, and serves to tweak its luminance. The magnitudes of the tweaks may be adjusted, at different locations, in accordance with a model of human visual perception—as applied to the host artwork at the locations where the tweak values will be applied. The tweak values are then summed with the pixel values of the host artwork. Many digital watermarks also convey a calibration signal. This signal (which can comprise a known signal in a transform domain, such as a sparse array of peaks (e.g., 30 to 120 peaks, and preferably 50-70) in the Fourier magnitude domain) enables a watermark detector to discern how an image submitted for decoding has been geometrically transformed since it was originally encoded. For example, the calibration signal (which may be called an orientation signal or reference signal) allows the detector to discern an amount by which the image has been shifted in X- and Y-directions (translation), an amount by which it has been changed in scale, and an amount by which it has been rotated. With knowledge of such "pose" information (geometric state information), the watermark detector can compensate for, e.g., counter-distort, the geometrical distortion of the image since its original watermarking, and can correctly extract the watermark payload.

In an exemplary system, each waxel corresponds to a 2×2 pixel neighborhood. A full watermark block thus spans an area of 256×256 pixels.

Within a 1280×960 pixel image frame captured by an industrial inspection camera, which 256×256 block of pixels should be examined, first, for presence of a watermark? Which should be examined second?

A 256×256 block can take an enormous number of possible locations within the image frame. (In particular, it can take (1280−256)*(960−256), or 720,896, different locations.) Given the speeds of industrial lines (and the still-faster speeds at which bursts of images may be captured), there is not time to consider even a small fraction of this number. Thus, it is essential to make best use of the watermark decoder's limited time.

To deal with this problem, one advantageous technique employed by Applicant is to sample exemplary test images of product running on the industrial line, and apply a variant of the principles detailed in Applicant's patent application 20160364623, to identify a prioritized sequence of candidate watermark locations that should be examined.

Each test image is exhaustively analyzed (off-line, without the time constraints of the operating industrial line) to determine which locations in the image frame most commonly have a decodable watermark signal.

Figure 9:
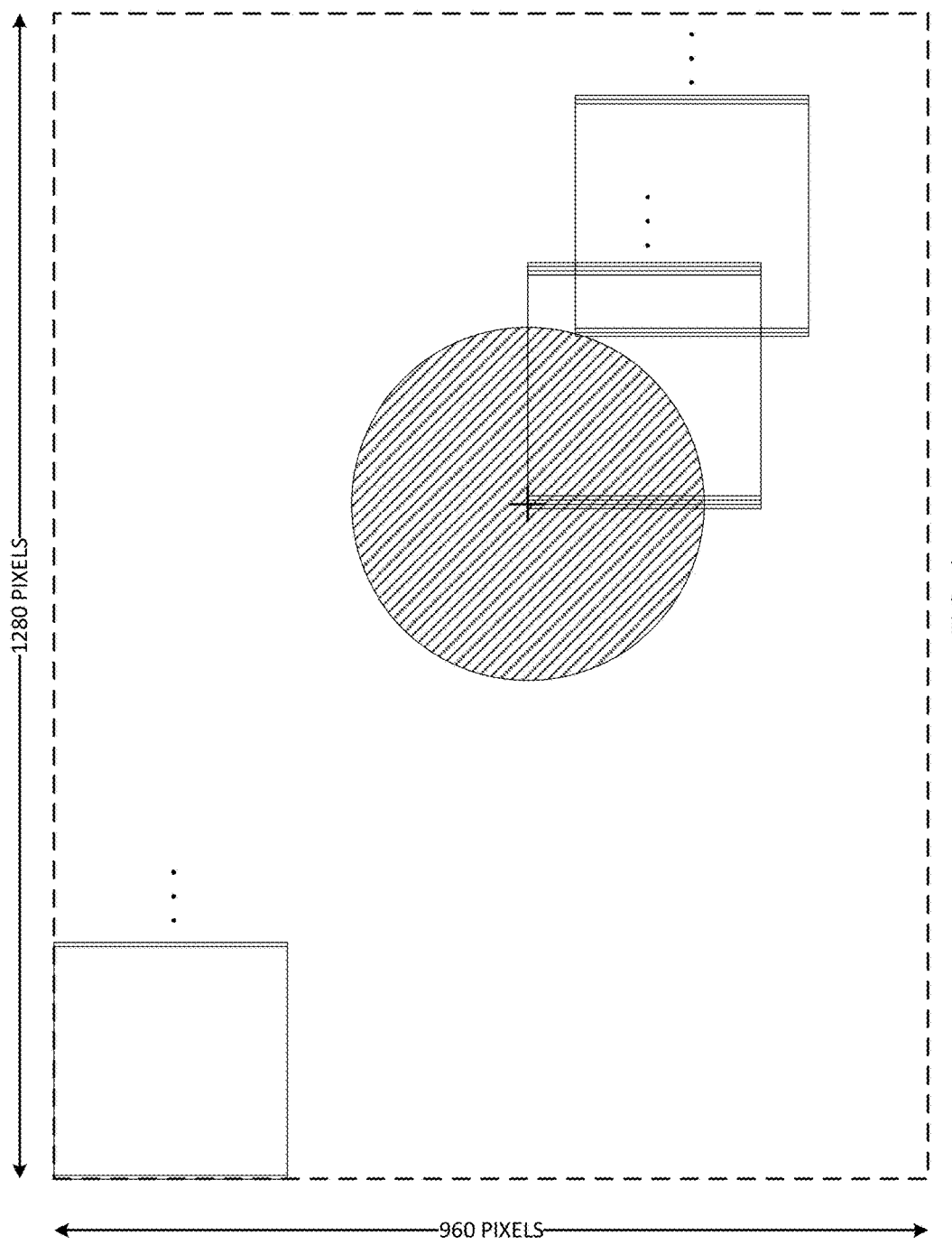

Referring to FIG. 9, the analysis can begin at the upper left corner of the image frame. A 256×256 pixel excerpt is tested to determine if a watermark payload can be extracted. The result (e.g., a "1" if a watermark can be extracted, else a "0") is written to a data structure. A second excerpt is then similarly-tested, spaced two pixels to the right of the first. And then likewise for a third, etc. This process continues until the upper left corner of the excerpt (which may be regarded as its anchor point, or origin) is at column 1022— the associated block then having spanned the full width of the 1280 pixel image frame. 512 image excerpts along the top of the frame have then been analyzed to determine if a watermark can be detected.

The process is repeated, across a second horizontal swath, 2 pixels below the first. 512 further image excerpts are thus analyzed. And likewise for third and further horizontal swaths, until the anchor point of the excerpted block has reached column 1022 in the 704$^{th}$ row of pixels.

A total of 180,224 different candidate watermark block locations are thereby analyzed within a single image frame, and the locations where a watermark was decoded are so-indicated in the data structure.

This process is then repeated with a second image frame, and a third image frame, for dozens, hundreds, or thousands of images. All of the data is compiled in the data structure.

Figure 10A:
FIGS. 10A and 10B illustrate use of a hit table to identify a ranked ordering of candidate blocks for watermark analysis.

FIG. 10A shows an illustrative data structure (which may be termed a "hit table"). Each row corresponds to a different image frame. Each column corresponds to a different pair of column/row coordinates identifying a particular 256×256 excerpt. A "1" or "0" in each cell indicates whether a watermark was decoded in that frame or not, in a block anchored by those coordinates.

From such a data structure, it is straightforward to find the candidate location within the set of sampled images that is most likely to have a decodable watermark signal. In the FIG. 10A example, this is the location anchored at column 738, and row 444. Across the 1000 images tested in this example, 917 images were found to have a decodable watermark in the 256×256 pixel excerpt anchored at this location.

If, during operation of the production line, the watermark decoder has sufficient time to examine a second candidate block of pixels for a watermark signal, the straightforward approach is to identify the column in FIG. 10A having the second-highest sum at its bottom. For example, the location at pixel coordinates {740,444} looks promising: 908 blocks at this location were found to be readable.

As detailed in cited publication 20160364623, however, Applicant has found this is rarely the best choice of a second block location. The reason is that the images having a decodable watermark at this second block location may be the images that were already successfully decoded by analysis of the first block location. The second block location should aim to decode a watermark from an image where the first block location failed to do so.

Thus, in picking a second candidate block location, all those images for which the first block location yielded a decodable watermark are removed from further consideration. Only the remainder are considered. Thus, referring to FIG. 10B, all the rows (images) in the hit table that had a "1" in the first-picked location (i.e., in the column headed by anchor pixel {738,444}) are greyed-out. Only the frames in which the first-picked location did not yield a successful watermark read are considered.

In a departure from publication 20160364623, other data are also removed from consideration. In particular, block locations that are "near" the first-chosen block location are removed from consideration—even from those images where the first-chosen block location was not found to contain a watermark.

"Near" can be set heuristically, based on the circumstances of particular applications. In the exemplary arrangement, two blocks are regarded as "near" if their anchor points are with a 192-pixel distance of each other. This is ¾ of the 256 pixel width blocks that are being examined. Other embodiments can naturally define "near" otherwise, such as within ½ of width of the blocks being examined, etc.

Referring to FIG. 9, a cross-hatched circle, of radius 192 pixels, is centered on the anchor point of the first candidate block location. Every block whose anchor point lies within this circle is removed from consideration as a second candidate block. This area may be considered a "keep-out" region for further block selection.

Similarly, in the hit table (FIG. 10B), each column whose anchor point is within a 192 pixel distance of the {738,444} anchor point of the first candidate block, is greyed-out and removed from consideration.

Figure 10B:

Thus, in choosing a second candidate block location, only the cells in the hit table (a) corresponding to frames where no watermark was read from the first candidate block location; and (b) corresponding to blocks that are more than a threshold distance away from the first candidate block, are considered. The contents of such cells are summed for each column. The column with the largest value indicates the pixel coordinates of the second candidate block. In FIG. 10B, this is the block anchored at pixel coordinates {924, 496}.

This same approach can be followed to identify third, fourth, and further candidate block locations. The images that were found to be watermark-decodable from a previously-determined candidate block location are removed from consideration. So are block locations that are near the previously-determined candidate block locations. The remaining data is tallied to determine which location offers the best prospect for watermark decoding.

In a particular embodiment, Applicant analyzed a large set of images captured from an industrial line packaging foodstuffs, and identified first, second, third, and fourth candidate block locations to examine, using the procedures detailed above. That system allowed time for six block locations to be examined. The final two locations were chosen based on analysis of the image content (so-called adaptive block selection), using the approach detailed in Applicant's published patent application 20150030201, and application Ser. No. 15/154,529, filed May 13, 2016 (now U.S. Pat. No. 10,217,182).

In some embodiments, if analysis of a candidate block yields a decoded watermark, further watermark analysis of that frame stops. Candidate blocks not yet analyzed are not analyzed. In other embodiments, all candidate blocks are analyzed. Several blocks may be found to have decodable watermarks. The payloads of the decodable watermarks may be identical (as when watermarks are found in two different regions of product artwork), or they may be different (as when a bottle of catsup has differently-watermarked front- and neck-labels).

When an object is expected to present multiple different watermarks (as in the catsup bottle with two labels case), data may be collected in two hit tables—a first identifying block locations at which the first watermark was detected, and a second identifying block locations at which the second watermark was detected. The first hit table can be processed, as detailed above, to identify candidate block locations that the system should examine first, second, third, etc., in its search for the first watermark, and the second hit table can be similarly processed to identify candidate block locations for the second watermark. In subsequent operation, the inspection system's available time budget is first allocated to looking at the top-ranked candidate locations for each watermark, followed by the second-ranked candidate locations, etc. After the top several candidate locations for each watermark have been evaluated, adaptive block selection techniques may be employed to identify other likely locations based on the attributes of particular image frames.

The foregoing discussion does not repeat various details of the basic diversity block selection arrangement, detailed in published application 20160364623, e.g., concerning analysis of affine-transformed counterparts of each image frame, etc. The reader is referred to that previous document, and should understand that each of the features detailed therein can be used in conjunction with the features detailed herein.

Single Frame Block Selection for Watermark Decoding

The above-detailed diversity block selection arrangement is premised on the availability of many images depicting watermarked products on the production line, from which statistically—useful data can be extracted. Sometimes, however, it is preferable (or necessary) to select candidate excerpts for watermark decoding based on a single frame depicting a watermarked product on the production line, e.g., so as not to delay start-up of the line by analyzing hundreds or thousands of images. Such arrangement (which may be termed a single frame block selection arrangement) is detailed next.

In this arrangement, like the diversity block selection arrangement, the inspection camera is aimed at the production line, and is set up to capture one or more image frames each time an object reaches a predetermined position. One such reference image frame depicting the object is captured during operation of the line, or during a preparatory, setup, phase of operation. Again, the aim is to decide, if circumstances permit watermark processing of only a single excerpt of each image thereafter captured during operation of the production line, which excerpt should be used? Or if circumstances permit two, three or four excerpts to be processed, which excerpts should they be? Which excerpts have the best chance of yielding successful watermark reads, based on the single reference image?

In an illustrative arrangement, plural overlapping blocks of imagery contained within the single frame of reference imagery are applied to a watermark detector, to identify a subset of N blocks from which digital watermark payload data can be successfully decoded. The overlapping blocks may be as depicted in FIG. 9, e.g., successively positioned across and down the image frame—each different than the preceding by one, or a few, pixels in the row and/or column dimensions (i.e., x- and/or y-translation).

As described above, many thousands of candidate pixel blocks are analyzed in FIG. 9. In accordance with one embodiment of the technology, x- and y-pixel coordinates for each block from which a watermark was successfully decoded, are stored in a data structure, and averaged, respectively, to yield a mean-x and mean-y value. These resultant mean values represent the spatial center-of-mass, so to speak, of the successfully-decoded watermark blocks.

The pixel coordinates used in such arrangement can be for the upper left corner of the block, for the center of the block, or for any other established location.

These mean-x and mean-y values define one candidate decoding location that can be applied to images subsequently captured during operation of the production line. From each such further image, an excerpt of pixels indicated by the {mean-x, mean-y} location within the captured image frame is submitted to a watermark decoder for processing.

While the just-described technique is suitable, a preferable technique exploits the factor that watermark strength across a block often is not uniform. For instance, the watermark signal may be stronger towards the left or right, or top or bottom, sides of a block, than in the center of the block. In accordance with a further embodiment, such spatial variation of watermark strength across each block is considered in selecting a candidate location within future images where watermark decoding should be attempted.

There are many methods that can be used to assess spatial variation of watermark strength. One is based on raw bit error rates.

As noted earlier, the watermark payload (e.g., of 64 bits) is error correction-coded to yield a 16,384 element sequence of raw bits, one bit of which is assigned to each element of the watermark block. The present method considers only those blocks from which a watermark is successfully decoded. (A 128×128 pixel block size is here assumed for expository convenience, i.e., with a waxel equating to a single pixel.) The raw bit sequence that was originally encoded into the block, and the placement of each of its bits within the block, can be recreated, since the decoded watermark reveals the payload and the block's affine parameters. These originally-encoded raw bits can be compared against the raw bit values actually detected from the block (after XORing with the noise sequence). This reveals which of the 16,384 elements of the 128×128 block have the correct raw bit, and which have an erroneous bit. The erroneous raw bits tend to group where the watermark signal is weaker; the correct raw bits tend to group where the watermark signal is stronger. The number of correct raw bits in N different M×M patches within the watermark block (e.g., 16 different 32×32 patches) can be counted, to serve as a relative measure of watermark strength at those patch locations. (These patches can overlap by one column (or row), or more. Or they may not overlap at all.) The center of the 32×32 patch having the highest count of correct raw bits may be taken as the location, within the 128×128 block, where the watermark strength is greatest (the "peak location within the block").

Rather than simply take the center of the 32×32 patch with the highest count of correct bits as the peak location within the block, Applicant prefers to employ a weighted average approach. That is, the center point coordinates of these patches are weighted by their respective number of correct raw bits (i.e., 0 to 1024) in computing a weighted average coordinate location within the block where the watermark signal is the strongest.

Once the peak locations within each of the successfully-decoded blocks is known, their positions can be averaged. This average location can serve as the center of a first candidate excerpt to be watermark-decoded in subsequent image frames. (In the discussion about candidate locations that follows, is should be understood that the candidate excerpt of imagery that is to be submitted for watermark decoding, is centered at the cited location. Repeated references to centering are thus avoided.)

Another method to determine the peak location within the block is based on localized strength of the calibration (reference) signal component of the watermark signal. Again, the analysis can proceed with reference to smaller patches, e.g., 32×32. For each, a metric indicating strength of the calibration signal is determined. This can be done by correlating a spatially-corresponding 32×32 pixel patch of the original calibration signal (represented in the spatial domain, instead of the Fourier magnitude domain in which it is typically defined) with each 32×32 image patch—after such patch has been counter-distorted to compensate for geometrical distortion of the captured image. The resulting correlation value is assigned to a location at the center of that 32×32 block. If this procedure is performed for each possible 32×32 pixel patch within the block, a 96×96 array of values results. This 96×96 array serves as a map of watermark strength—with higher values indicating centers of 32×32 patches having stronger watermark calibration signals.

The center of the 32×32 patch having the highest correlation with the calibration signal may be taken as the peak location within the block. But Applicant prefers, instead, to weight the x- and y-coordinates of the center of each 32×32 patch, with that patch's correlation value, and determine a spatial average of such weighted coordinates. This weighted average location within the 128×128 block then serves as the peak location.

This arrangement may be further enhanced by "oct-axis" filtering the reference frame from which the 128×128 block is identified, and from which the 32×32 patches are identified, prior to performing the correlation on the 32×32 pixel patches. Oct-axis filtering is reviewed in the next section, entitled "Non-Linear Filtering, and is further discussed in documents incorporated by reference. (Oct-axis filtering attenuates the host imagery, improving the signal to noise ratio of the subtle watermark signal.( In other arrangements, not all possible 32×32 pixel patches within the 128×128 pixel block are considered. Instead of each patch overlapping an adjoining patch by 31 columns (or 31 rows), the patches can be selected at intervals of 2 columns (rows), or 4 or 8 or 16 or even 32 columns (rows). In this last arrangement, just 16 32×32 patches within the 128×128 block are considered—none overlapping.

Figures 11A, 11B:
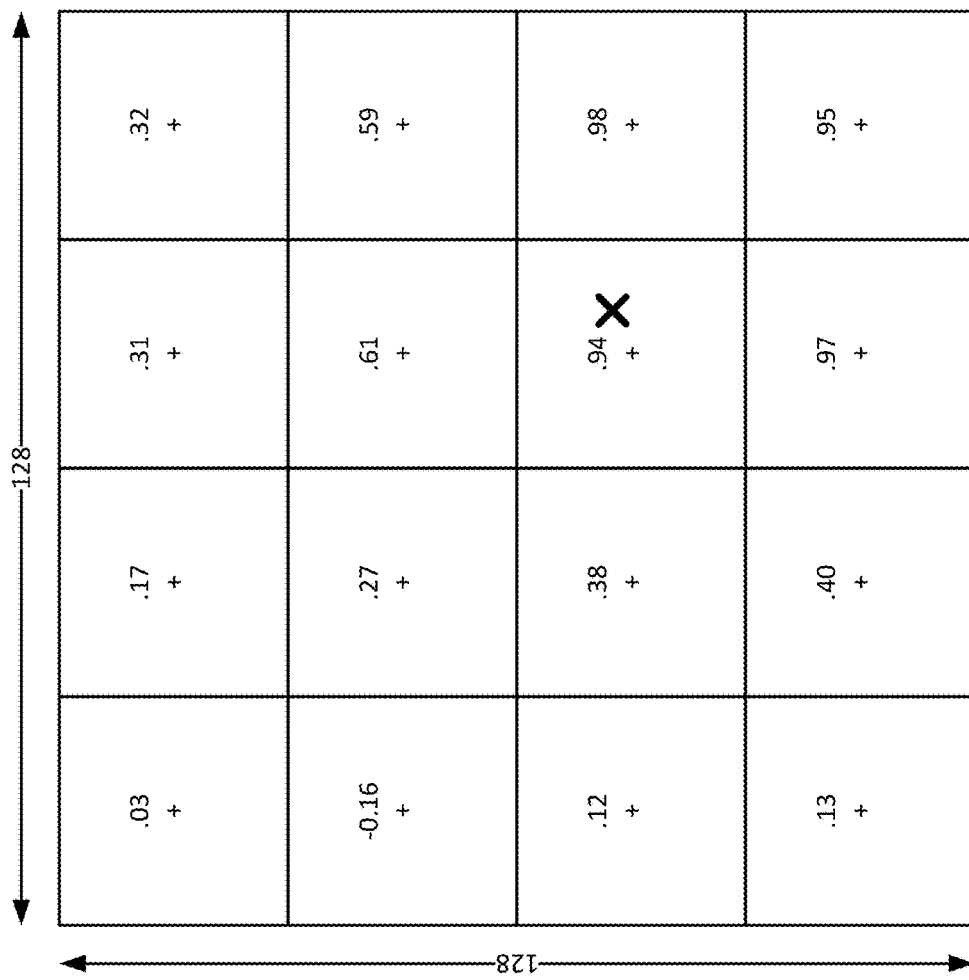
FIGS. 11A and 11B illustrate one particular method to assess spatial variation of watermark strength.

FIG. 11A shows this last arrangement—16 32×32 patches tiled across a 128×128 block. Each patch is labeled with the value resulting from correlation of the oct-axis-filtered pixel patch with a corresponding spatial domain patch of the calibration signal. The dark "X" indicates the calculated position of the strongest watermark signal, the peak location within the block, using the weighted spatial average approach detailed above. FIG. 11B shows the weighted spatial averaging math that led to the dark "X" being positioned at coordinates (86,78).

Again, the thus-determined peak locations, for each of the successfully-decoded watermark blocks within the reference image, can be averaged to yield an overall-best candidate location. An image excerpt at this location can be processed from each inspection camera frame that is thereafter captured during operation of the production line.

Applicant has found that rather than simply averaging the peak watermark signal strength locations within each block (regardless of how determined), it is preferable to consider the spatial density of these peak locations.

Figure 12:
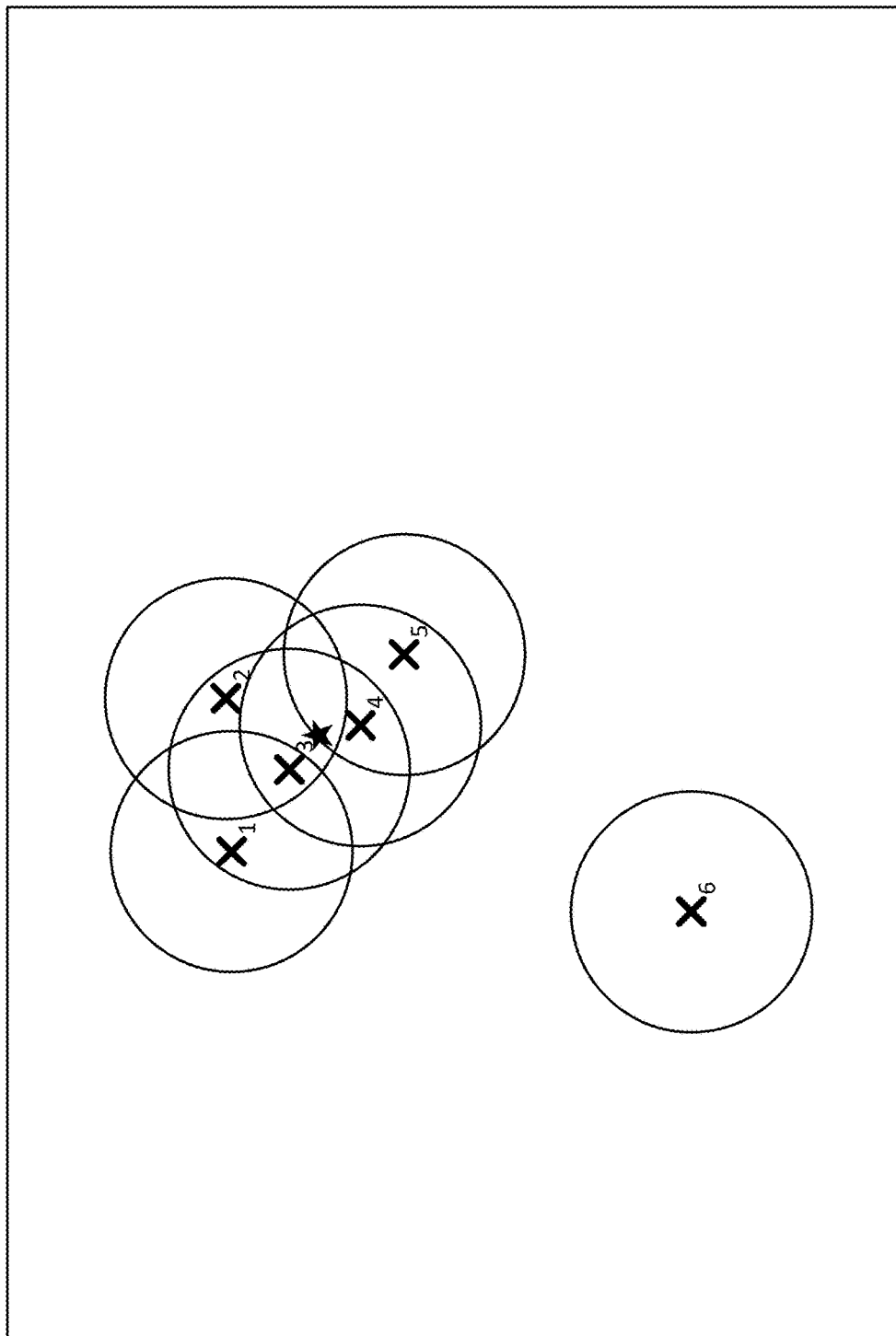
FIG. 12 shows peak locations of successfully-decoded watermark blocks in a reference image frame 90, and neighboring regions around such peaks.

Referring to FIG. 12, the dark "X" marks indicate peak locations of some of the successfully-decoded watermark blocks in the reference image frame 90. Around each peak is drawn a circle, indicating a surrounding neighborhood in the image frame. The circle may have a diameter of 128 pixels.

In accordance with this aspect of the technology, each peak is associated with a neighbor count that indicates the number of other peaks within the surrounding neighborhood. The neighborhood around peak 1 includes one other peak (peak 3), so peak 1 is assigned a neighbor count of 1. The neighborhood around peak 2 encompasses one other peak (peak 3), so peak 2 is also assigned a count of 1. In similar fashion, peak 3 has a count of 3, peak 4 has a count of 2, peak 5 has a count of 1, and peak 6 has a count of 0.

An image excerpt centered on the peak having the highest neighbor count, of all peaks in all watermark-decoded blocks of the reference image, can be a first candidate for watermark decoding in processing of subsequent images captured from the production line.

Alternatively or additionally, within a block, each peak's x- and y-coordinates can be weighted by its corresponding neighbor count value, and averaged to determine a count-weighted average of the block's peak locations (in a manner analogous to that depicted in FIG. 11B). The result is shown by the black star in FIG. 12. After performing such operation on all blocks from which a watermark was decoded, a best block is selected. The best block can be determined by summing the neighbor count values for all peaks within each block. The block with the highest sum is deemed best. Within that block, the just-determined count-weighted average of its peak locations can serve as the location of a candidate image excerpt for watermark decoding.

A further variant is to not count all neighboring peaks equally. Instead, peaks that are positioned closer to the center of a neighborhood are counted more than peaks that are further away. That is, a distance-dependent function can be applied. Any function that diminishes with distance can be employed, e.g., linear, Gaussian, etc.

Figure 13:
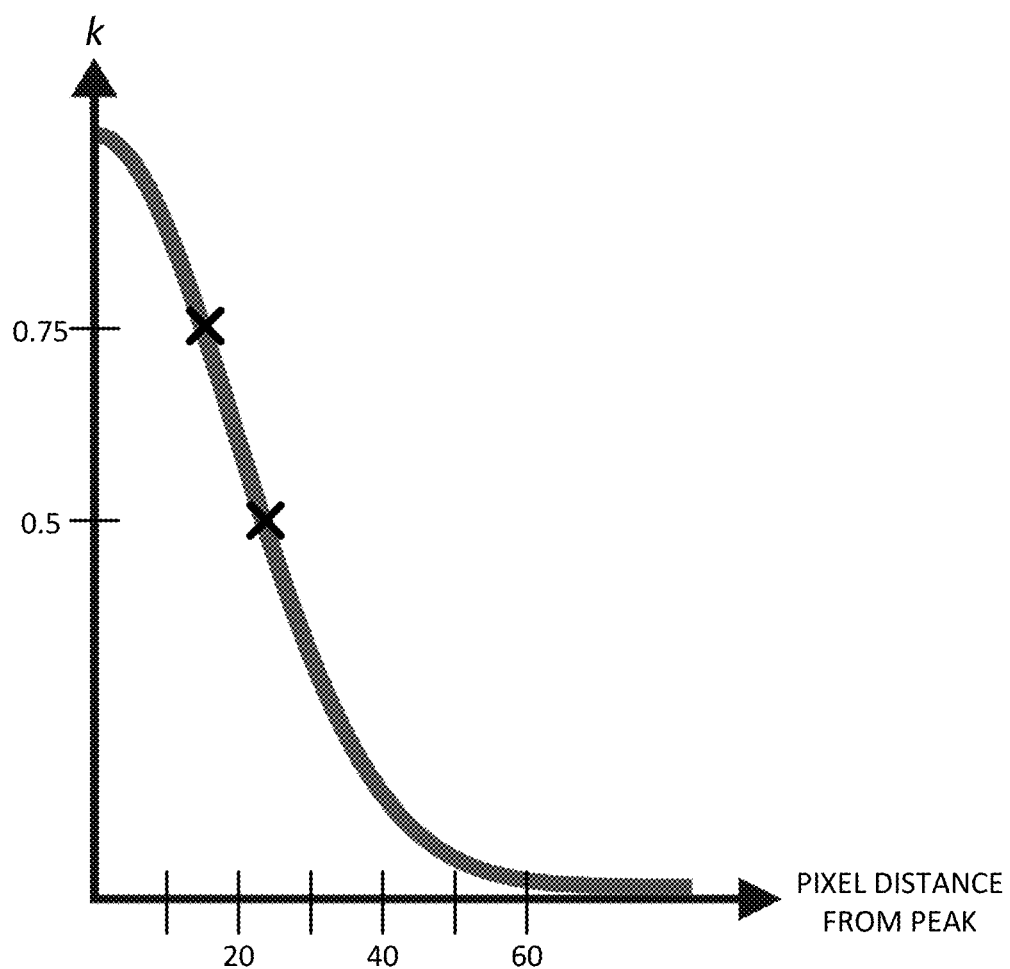
FIG. 13 illustrates the concept of incrementing a neighbor count by a distance-dependent factor.
Figure 17:
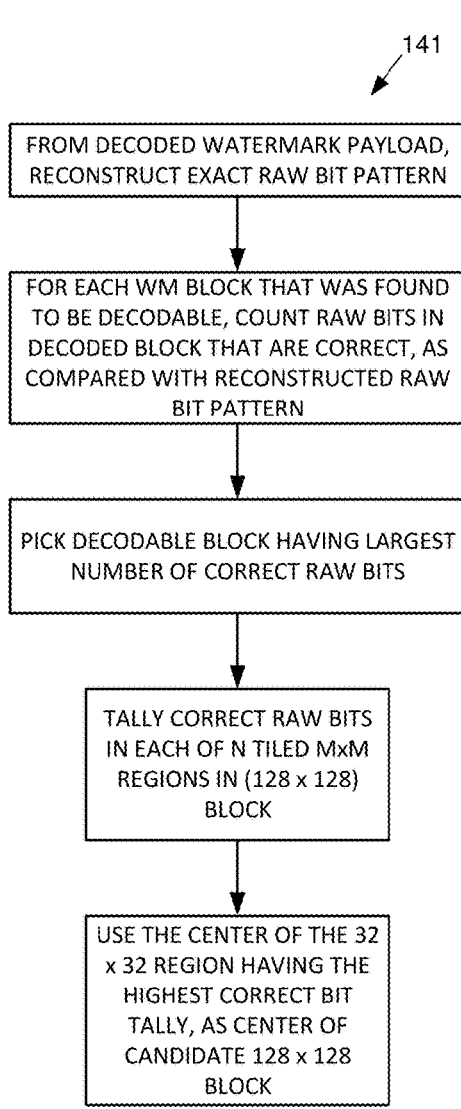
Figure 18:
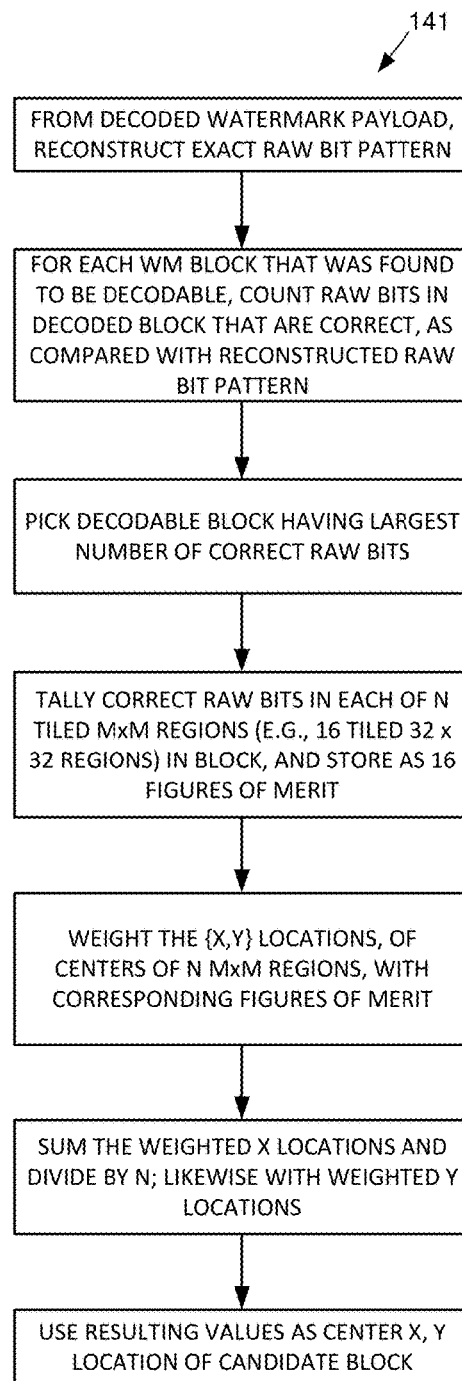
Figures 19, 20:
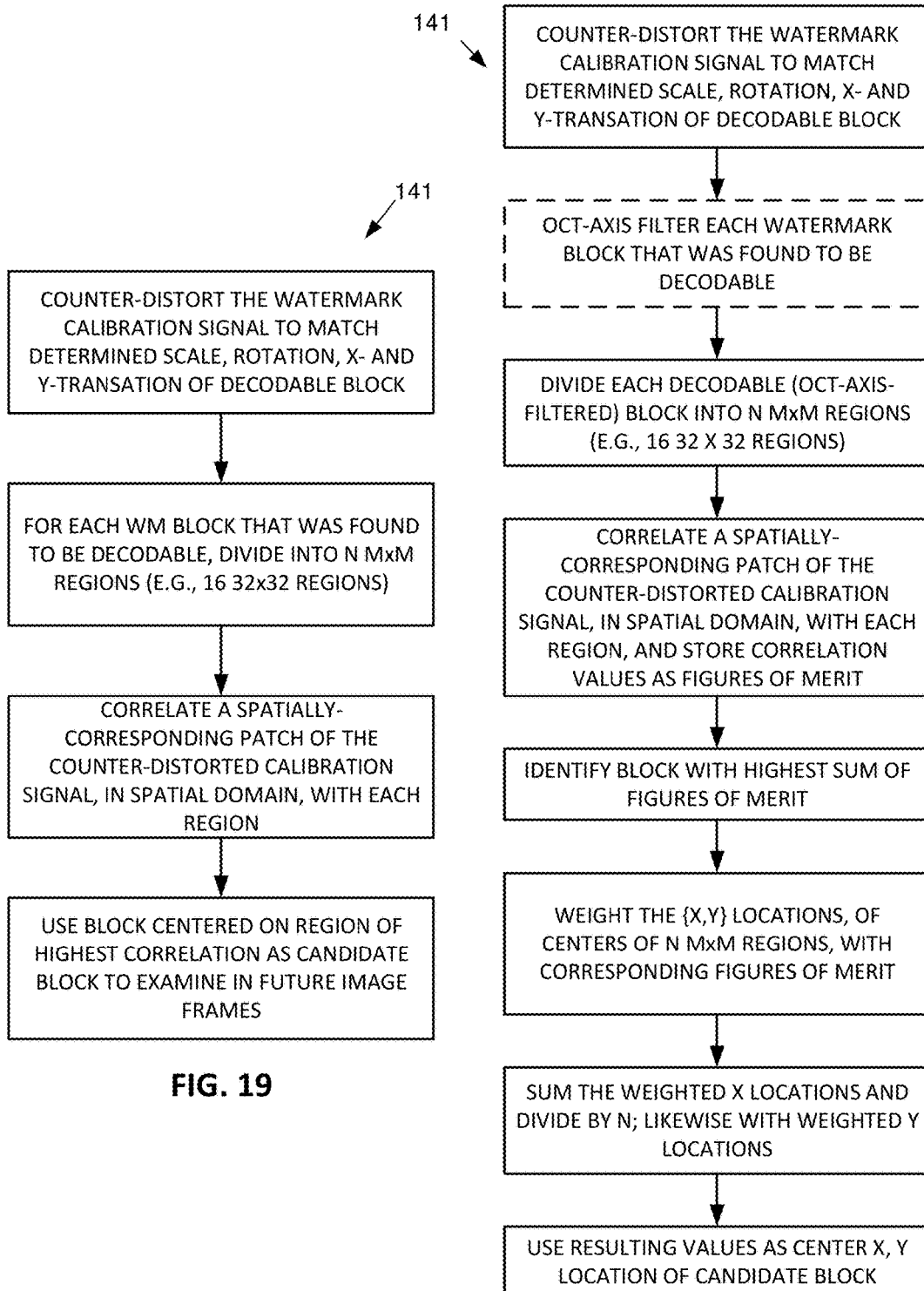
Figure 25:
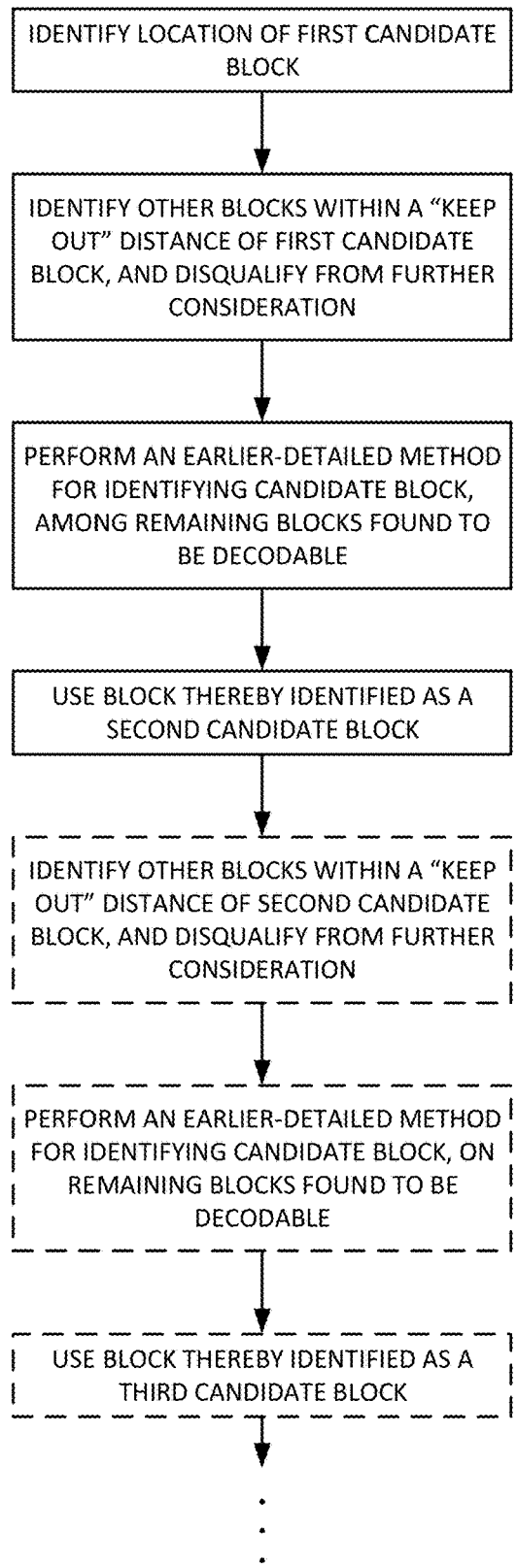
FIG. 25 is a flow chart detailing an algorithm according to another aspect of the present technology

FIG. 13 illustrates the concept with a Gaussian curve, centered on a block's peak location. Two peaks are in the circular neighborhood: one is 15 pixels away, and one is 23 pixels away. The first does not increment the neighbor count by 1, but rather by 0.75. The second increments the neighbor count by only 0.5. So instead of a neighbor count of 2, this peak has a count of 1.25. Such arrangement further emphasizes closely-neighboring peaks in determining a candidate decoding location.

The one peak in the reference frame with a maximum distance-dependent neighbor count, can be used as a first candidate decoding location. An average of peak locations, weighted by such distance-dependent counts, in the block having the largest sum of distant-dependent neighbor counts, can be used as a second candidate decoding location.

It will be recognized that the above-described first and second candidate decoding locations may be close to each other. This reduces some of the advantages of having two decoding locations, since the watermark decoding results from one area will tend to correlate with results from nearby areas.

To force the first and second candidate decoding locations somewhat away from each other, the "keep-out" region discussed above, in connection with FIG. 9, can be employed. That is, once a first candidate decoding location is determined, a surrounding region can be defined in which the second candidate decoding location should not be placed. For example, a circular region, e.g., of radius 128 pixels, around the first candidate decoding location can define the keep-out region. Further decoding candidates within that region can be disqualified from consideration.

FIGS. 14-25 are flowcharts expressing aspects and variations of the algorithms detailed above. FIGS. 15-24, for example, details alternative sub-algorithms that may be used for block 141 in FIG. 14. Such algorithms and sub-algorithms can be implemented in various forms, e.g., in software executing on conventional computer system hardware, or in custom hardware, etc., as further detailed below.

While this discussion has generally referred to blocks and patches in terms of pixels, the detailed operations are more typically performed on the basis of "waxels," as was previously noted. A waxel may be the same as a pixel. Or it may be a region of 2×2 pixels, 3×3 pixels, 4×4 pixels, etc.

In an illustrative embodiment, each watermark block is originally encoded and printed on the object artwork (e.g., label or carton) so that each of the 128×128 "waxels" comprising the block is represented by a 4×4 area of pixels, at 300 dpi (i.e., with the printed block spanning 512 pixels, or 1.70 inches, on a side).

If the watermark block that is sensed by the inspection camera similarly spans a region that is 512 camera pixels on a side, the watermark is said to be sensed at a scale of 1.0. If the block spans a regions that is 256 camera pixels on a side, the camera is viewing the object from a greater distance; the watermark is said to be sensed at a scale of 2.0. Etc.

Watermark detectors typically expect to receive camera imagery for decoding at roughly the same resolution as the original, printed version (e.g., with a watermark block spanning 512 camera pixels on a side). The detector can then average each 4×4 area of pixels to yield a 128×128 block, i.e., down-sampling by 4. (In practice, most watermark decoders can work with a range of block sizes, from 50% to 200% of nominal.)

If the camera-captured imagery represents watermark blocks at a resolution smaller than 512 camera pixels on a size, then the image may be down-sampled by a different value to yield a 128×128 set of data for watermark decoding. If the camera-captured imagery represents watermark blocks at a resolution of 128 pixels on a side, then no down-sampling may be applied.

In one embodiment of the present technology, the above-detailed operations are performed initially at scale 1—anticipating that watermarked image blocks in the captured imagery are represented at roughly 512×512 pixels. Down-sampling by 4 is applied to yield blocks of roughly 128×128 pixels. However, the watermark scale in the captured imagery is not known in advance. Accordingly, in a further aspect of the present technology, the above-detailed procedures for identifying candidate block locations are repeated—each time on the reference frame after down-sampling value with a different value. In one particular embodiment, in addition to down-sampling by 4, down-sampling by 1, 2, 3, 5 and 6 are also tried. The measures discussed above are re-computed on each resulting down-sampled reference image frame, and the down-sampling value that yields the best results (with the block location(s) indicated in that down-sampled reference frame) is used in processing subsequent image frames.

(In comparing results between differently-down-sampled reference frames, some adjustments may be made to ensure valid comparisons. For example, in a 1280×960 captured image frame that is down-sampled by 1 (i.e., no down-sampling), there are (1280−128)*(960−128)=958,464 different 128×128 waxel blocks that may be successfully decoded, or not. If the reference frame is, instead, down-sampled by 4, there are (320−128)*(240−128)=21,504 different 128×128 waxel blocks that may be successfully decoded, or not. This is a difference of roughly 44:1. Thus a measurement, such as the number of other peaks within a neighborhood of 64 waxels around a center peak, can be expected to be much greater when down-sampling by 1, than when down-sampling by 4—simply because there are more blocks involved. A corresponding normalization factor should thus be applied to one measure (e.g., the number of neighboring peaks with down-sampling of 1) to assure a meaningful comparison with another measure (e.g., the number of neighboring peaks with down-sampling of 4).)

To recap so-far, a reference image frame is captured, depicting an object on the production line. Counterpart blocks, at different down-sampling values, are determined, and are analyzed to identifying promising locations from which imagery in later-captured image frames can be submitted for watermark decoding. If circumstances permit only a single image excerpt to be analyzed in each later frame, its location may be that of the peak location (as described above), having the greatest distance-weighted count. If circumstances permit a second excerpt to also be analyzed, its location may be in a block having the greatest sum of distance-dependent counts. Within that block, the decoding location can be placed at the average of the determined peak locations, weighted by their respective distance-dependent counts.

If circumstances allow for identification of third or following candidate decoding locations, Applicant prefers next to try applying various affine warps to the image frames, to counteract affine distortion that may be present in the imagery captured by the inspection camera.

For example, if the object—when imaged by the camera—has its largest face not squarely facing the camera, but tilted away by 10 or 30 degrees, better results will typically be achieved by processing the captured imagery so as to un-do, or at least reduce, the apparent distortion of the object as depicted in the captured imagery. (The following methods operate on the down-sampled version of the reference signal from which the first candidate decoding location was identified; other down-sampling values are typically not considered.)

In accordance with this aspect of the present technology, the reference image frame is manipulated to produce a variety of different affine-transformed counterparts. Considering a cereal box as the object, it may be positioned so that the front face is tilted 10° to the right (i.e., with the right edge of the face further from the camera than the left edge). It may also be positioned so that the front face is tilted 10° backwards (i.e., the top edge of the face further from the camera than the bottom edge). Or it may be tilted, relative to the camera, in an intermediate fashion, with the upper right corner tilted 10° away from the camera. Likewise for five other tilts: towards the upper left corner, towards the left, towards the lower left corner, towards the bottom, and towards the lower right corner. In each such depiction, the more remote edge(s) of the box are foreshortened in the captured imagery. For each such possibility, a counter-distortion is applied to the captured reference frame of imagery to restore it to an approximately rectilinear view, with the opposite edges of the box being the same length, parallel to each other, and at right angles to the adjoining edges.

Similar counterparts can be generated for other values of tilts, e.g., 20°, 30°, 40° and 50°.

The number of such differently affine-transformed image counterparts that are produced from the reference frame depend on the requirements and constraints of the particular application. Commonly there are two or more, and in some applications there may be 20 or more.

The above-detailed methods for identifying candidate decoding locations are then applied to each of these affine-distorted counterparts. In a particular embodiment, the peak location having the greatest distance-weighted count, among all watermark-decoded blocks, among all affine-transformed reference images, serves as a further (e.g., a third) candidate location. For instance, if the peak with the greatest distance-weighted neighbor count is found in a reference image that has been affine-transformed to counteract a 20 degree tilt to the right, then subsequent images are similarly affine-transformed, and an image excerpt at the location corresponding to that peak is selected for watermark decoding in such transformed images.

If circumstances permit a further (e.g., a fourth) excerpt also to be analyzed, a "best" affine-transformed image is identified by tallying, for each image, its total distance-dependent neighbor counts. Within that affine-transformed image, a best block is next selected, similarly, i.e., the block having the greatest tally of distance-dependent neighbor counts. The fourth excerpt is then placed at the average of the peak locations in this block, weighted by the peaks' respective distance-dependent counts.

By the arrangements detailed above, a system can identify one, or a few, high-probability strategies for successfully extracting a watermark payload from imagery of objects in a production system, within the tight time (and often processing power) constraints of such environments—optimizing use of available resources.

Non-Linear Filtering

In some of the detailed arrangements, the human-visible artwork on the object interferes with decoding of the subtle watermark signal. To reduce the influence of the artwork on watermark decoding, various forms of non-linear filtering can be applied to imagery.

In one, the value of each captured image pixel is transformed by subtracting a local average of nearby pixel values. In another, each pixel is assigned a new value based on some function of the original pixel's value, relative to its neighbors. An exemplary embodiment considers the values of eight neighbors—the pixels to the north, northeast, east, southeast, south, southwest, west and northwest. One such function counts the number of neighboring pixels having lower pixel values, offset by the number of neighboring pixels having higher pixel values. Each pixel is thus reassigned a value between −8 and +8. (These values may all be incremented by 8 to yield non-negative values, yielding output pixel values in the range of 0-16. Such technology is detailed in Digimarc's U.S. Pat. Nos. 6,580,809, 6,724,914, 6,631,198, 6,483,927, 7,688,996 and publications 20100325117 and 20100165158, where it is sometimes referenced as "oct-axis" or predictive filtering.)

CONCLUDING REMARKS

Having described and illustrated principles of the technology with reference to certain embodiments, it should be recognized that the technology is not so-limited.

For example, while the foregoing description has focused on watermark detection, the artisan will recognize that the detailed arrangements can also be used advantageously in extracting information from imagery by other techniques, such as by optical character recognition (OCR), barcode decoding, image fingerprint recognition (e.g., by SIFT, bag-of-features techniques, etc.), and recognition by neural networks (e.g., convolutional neural networks, as detailed in Applicant's pending patent application Ser. No. 15/726,290, filed Oct. 5, 2017).

Similarly, while aspects of the foregoing description particular considered parameters of exposure interval, lens aperture, and camera gain, it should be understood that the same principles can be applied with other parameters. (One such alternative parameter is the intensity of supplemental illumination projected onto the projection line, as by a flash or flood lamp. Another is the duration of such supplemental illumination, e.g., flash interval.)

In the arrangements detailed above for identifying a ranked list of candidate image excerpts for watermark decoding, there may be instances in which two locations under consideration yield identical metrics. In such case, a heuristic can be employed to break the tie, such as selecting the location that is closest to the center of the camera frame, or selecting the location that is most remote from the location(s) previously selected as candidates.

Sometimes something changes during the course of a production run, and candidate decoding locations that formerly produced reliable reads no longer do so. In accordance with another aspect of the present technology, one of the above-described block identification processes is automatically triggered whenever a threshold number of objects fails to generate a watermark read. The process can be executed as a background process, and can update the candidate locations used, once completed.

Similarly, even if watermark decoding appears to be occurring properly, a new set of test images (for the diversity block selection arrangement), or a new reference image (for the single frame block selection arrangement) can be sampled occasionally, and one of the foregoing processes repeated during ongoing operation of the industrial line, to ensure that there is not a different set of candidate block locations that might be better than those presently in use.

Although the single frame block selection arrangement was described in connection with a single reference image, the detailed principles can be applied to a burst of plural images captured when the object passes a trigger location—each depicting the object at a different position in the frame. Such technique can examine each image using the detailed criteria, and identify the best image frame, and the most promising location(s) within that frame, to try for watermark decoding in later image bursts. Or, plural images, each depicting a different object instance at a consistent position along the production line, can be analyzed in the detailed manner, and a consensus decision can be made based on the candidate location results thereby achieved.

The single frame selection arrangement detailed using one selection criterion to identify a first candidate decoding location, using a different one to identify a second candidate decoding location, etc. In other embodiments, different criteria need not be used to identify different decoding locations. For example, a top-ranked location by a first criterion can establish a first candidate decoding location, and a second-ranked location by that same criterion can establish a second candidate decoding location, etc. Thus, each of the detailed selection criteria can be employed to identify none, one, some, or all, of the candidate decoding locations.

Features described in connection with one technique for identifying candidate decoding locations can generally be employed in connection with a different technique. One example was noted above—the "keep-out" region that was originally described in connection with the diversity block selection arrangement is similarly applicable to the single frame block selection arrangement. Many others were not particularly called-out, but will be understood from the specification by artisans (including the consideration of different down-sampling values, and different affine distortions, in the diversity block selection arrangement).

Naturally, the particular numeric values detailed above are exemplary, and should not be taken as limiting the scope of the technology. An image frame may be any size. A watermark block needn't be 128×128 waxels. A waxel needn't be a 2×2 pixel region. Etc., etc.

Although the above examples employed a single watermark detector, e.g., to successively examine multiple frames of image data, it should be recognized that multiple watermark detectors can run simultaneously, e.g., on different cores of a multi-core processor. Thus, in a burst mode image capture, Image3 may be submitted for decoding on Core3, while Image2 is being watermark-decoded by Core2, and Core1 is outputting results from its decoding of Image1.

While the emphasis of the foregoing description has been on implementations in a production line, it will be recognized that the principles of this technology finds utility in various different contexts, including other industrial applications (e.g., warehouse management and e-commerce fulfillment), retail (e.g., point of sale scanners at grocery stores) and consumer (e.g., in connection with smartphones).

Although the Shannon entropy metric is detailed in one of the above arrangements, other measures can be substituted. For example, a KL (Kullback-Leibler) divergence can be computed instead. More generally, any measure of difference (or similarity) between an actual probability distribution (e.g., of pixel values) and an idealized probability distribution, can be employed. As noted, an idealized distribution of pixel values in the case of a linear gradient target, imaged by a 1.228 megapixel sensor, is 4800 pixels of each value, between 0 and 255. Thus, for example, any measure of distance between such ideal distribution (e.g., expressed as a histogram), and the distribution found in a captured frame of the gradient target, can be employed. Whether the measure is maximized or minimized depends on the particular measure employed (e.g., the Shannon metric is maximized; a divergence metric is minimized).

Suitable inspection cameras are available from Cognex Corporation, e.g., cameras in its Dataman 200, 300 and 360 series.

Computing devices suitable to perform the processes detailed herein are familiar to the artisan. In general terms, each may include one or more processors, one or more memories (e.g. RAM), storage (e.g., a disk or flash memory), a user interface (which may include, e.g., a keypad, a TFT LCD or OLED display screen, touch or other gesture sensors, one or more microphones, etc., together with software instructions for providing a graphical user interface), interconnections between these elements (e.g., buses), and an interface for communicating with other devices (which may be wireless, such as GSM, 3G, 4G, CDMA, WiFi, WiMax, Zigbee or Bluetooth, and/or wired, such as through an Ethernet local area network, etc.).

The arrangements detailed above can be implemented using a variety of different hardware structures, including a microprocessor, an ASIC (Application Specific Integrated Circuit) and an FPGA (Field Programmable Gate Array). Hybrids of such arrangements can also be employed, such as reconfigurable hardware, and ASIPs.

By microprocessor, Applicant means a particular type of hardware structure, namely a multipurpose, clock-driven, integrated circuit that includes both integer and floating point arithmetic logic units (ALUs), control logic, a collection of registers, and scratchpad memory (aka cache memory), linked by fixed bus interconnects. The control logic fetches instruction codes from a memory (often external), and initiates a sequence of operations required for the ALUs to carry out the instruction code. The instruction codes are drawn from a limited vocabulary of instructions, which may be regarded as the microprocessor's native instruction set.

A particular implementation of the above-detailed arrangements on a microprocessor involves first defining a sequence of algorithm operations in a high level computer language, such as MatLab or C++ (sometimes termed source code), and then using a commercially available compiler (such as the Intel C++ compiler) to generate machine code (i.e., instructions in the native instruction set, sometimes termed object code) from the source code. (Both the source code and the machine code are regarded as software instructions herein.) The process is then executed by instructing the microprocessor to execute the compiled code.

As noted, many microprocessors are now amalgamations of several simpler microprocessors (termed "cores"). Such arrangements allow multiple operations to be executed in parallel. (Some elements—such as the bus structure and cache memory may be shared between the cores.)

Examples of microprocessor structures include the Intel Xeon, Atom and Core-I series of devices. They are attractive choices in many applications because they are off-the-shelf components. Implementation need not wait for custom design/fabrication.

Closely related to microprocessors are GPUs (Graphics Processing Units). GPUs are similar to microprocessors in that they include ALUs, control logic, registers, cache, and fixed bus interconnects. However, the native instruction sets of GPUs are commonly optimized for image/video processing tasks, such as moving large blocks of data to and from memory, and performing identical operations simultaneously on multiple sets of data (e.g., pixels or pixel blocks). Other specialized tasks, such as rotating and translating arrays of vertex data into different coordinate systems, and interpolation, are also generally supported. The leading vendors of GPU hardware include Nvidia, ATI/AMD, and Intel. As used herein, Applicant intends references to microprocessors to also encompass GPUs.

GPUs are attractive structural choices for execution of the detailed algorithms, due to the nature of the data being processed, and the opportunities for parallelism.

While microprocessors can be reprogrammed, by suitable software, to perform a variety of different algorithms, ASICs cannot. While a particular Intel microprocessor might be programmed today to compute a Shannon entropy metric, and programmed tomorrow to prepare a user's tax return, an ASIC structure does not have this flexibility. Rather, an ASIC is designed and fabricated to serve a dedicated task, or limited set of tasks. It is purpose-built.

An ASIC structure comprises an array of circuitry that is custom-designed to perform a particular function. There are two general classes: gate array (sometimes termed semi-custom), and full-custom. In the former, the hardware comprises a regular array of (typically) millions of digital logic gates (e.g., XOR and/or AND gates), fabricated in diffusion layers and spread across a silicon substrate. Metallization layers, defining a custom interconnect, are then applied—permanently linking certain of the gates in a fixed topology. (A consequence of this hardware structure is that many of the fabricated gates—commonly a majority—are typically left unused.)

In full-custom ASICs, however, the arrangement of gates is custom-designed to serve the intended purpose (e.g., to perform a specified algorithm). The custom design makes more efficient use of the available substrate space—allowing shorter signal paths and higher speed performance. Full-custom ASICs can also be fabricated to include analog components, and other circuits.

Generally speaking, ASIC-based implementations of the detailed algorithms offer higher performance, and consume less power, than implementations employing microprocessors. A drawback, however, is the significant time and expense required to design and fabricate circuitry that is tailor-made for one particular application.

An ASIC-based particular implementation of the above-detailed methods again begins by defining a sequence of algorithm operations in a source code, such as MatLab or C++. However, instead of compiling to the native instruction set of a multipurpose microprocessor, the source code is compiled to a "hardware description language," such as VHDL (an IEEE standard), using a compiler such as HDL-Coder (available from MathWorks). The VHDL output is then applied to a hardware synthesis program, such as Design Compiler by Synopsis, HDL Designer by Mentor Graphics, or Encounter RTL Compiler by Cadence Design Systems. The hardware synthesis program provides output data specifying a particular array of electronic logic gates that will realize the technology in hardware form, as a special-purpose machine dedicated to such purpose. This output data is then provided to a semiconductor fabrication contractor, which uses it to produce the customized silicon part. (Suitable contractors include TSMC, Global Foundries, and ON Semiconductors.)

A third hardware structure that can be used to execute the above-detailed algorithms is an FPGA. An FPGA is a cousin to the semi-custom gate array discussed above. However, instead of using metallization layers to define a fixed interconnect between a generic array of gates, the interconnect is defined by a network of switches that can be electrically configured (and reconfigured) to be either on or off. The configuration data is stored in, and read from, a memory (which may be external). By such arrangement, the linking of the logic gates—and thus the functionality of the circuit— can be changed at will, by loading different configuration instructions from the memory, which reconfigure how these interconnect switches are set.

FPGAs also differ from semi-custom gate arrays in that they commonly do not consist wholly of simple gates. Instead, FPGAs can include some logic elements configured to perform complex combinational functions. Also, memory elements (e.g., flip-flops, but more typically complete blocks of RAM memory) can be included. Likewise with A/D and D/A converters. Again, the reconfigurable interconnect that characterizes FPGAs enables such additional elements to be incorporated at desired locations within a larger circuit.

Examples of FPGA structures include the Stratix FPGA from Altera (now Intel), and the Spartan FPGA from Xilinx.

As with the other hardware structures, implementation of each of the above-detailed algorithms begins by authoring the algorithm in a high level language. And, as with the ASIC implementation, the high level language is next compiled into VHDL. But then the interconnect configuration instructions are generated from the VHDL by a software tool specific to the family of FPGA being used (e.g., Stratix/Spartan).

Hybrids of the foregoing structures can also be used to perform the detailed algorithms. One structure employs a microprocessor that is integrated on a substrate as a component of an ASIC. Such arrangement is termed a System on a Chip (SOC). Similarly, a microprocessor can be among the elements available for reconfigurable-interconnection with other elements in an FPGA. Such arrangement may be termed a System on a Programmable Chip (SORC).

Another hybrid approach, termed reconfigurable hardware by the Applicant, employs one or more ASIC elements. However, certain aspects of the ASIC operation can be reconfigured by parameters stored in one or more memories. For example, a watermark calibration signal can be defined by parameters stored in a re-writable memory. By such arrangement, the same ASIC may be incorporated into two disparate devices, which employ different watermark calibration signals. One may be an industrial inspection system for reading watermark-encoded identifiers from objects on a manufacturing line, which looks for a calibration signal comprised of one particular constellation of spatial frequency signals. A second may be an age verification terminal (e.g., at a liquor store) for reading watermark-encoded birthdate information hidden in a driver's license—which looks for a calibration signal comprised of a second, different constellation of spatial frequency signals. The chips are all identically produced in a single semiconductor fab, but are differentiated in their end-use by different calibration signal data stored in memory (which may be on-chip or off).

Yet another hybrid approach employs application-specific instruction set processors (ASIPS). ASIPS can be thought of as microprocessors. However, instead of having multipurpose native instruction sets, the instruction set is tailored—in the design stage, prior to fabrication—to a particular intended use. Thus, an ASIP may be designed to include native instructions that serve operations prevalent in a particular application (e.g., oct-axis computation). However, such native instruction set would typically lack certain of the instructions available in more general purpose microprocessors.

Reconfigurable hardware and ASIP arrangements are further detailed in patent published patent application 20170004597, the disclosure of which is incorporated herein by reference.

Software instructions for implementing the detailed functionality can be authored by artisans without undue experimentation from the descriptions provided herein, e.g., written in C, C++, MatLab, Visual Basic, Java, Python, Tcl, Perl, Scheme, Ruby, etc., in conjunction with associated data.

Software and hardware configuration data/instructions are commonly stored as instructions in one or more data structures conveyed by tangible media, such as magnetic or optical discs, memory cards, ROM, etc., which may be accessed across a network.

Different of the functionality can be implemented on different devices. Thus, it should be understood that description of an operation as being performed by a particular device (e.g., a computer in a food packaging facility) is not limiting but exemplary; performance of the operation by another device (e.g., a cloud computer), or shared between devices, is also expressly contemplated.

In like fashion, description of data being stored on a particular device is also exemplary; data can be stored anywhere: local device, remote device, in the cloud, distributed, etc.

In addition to the patent documents referenced elsewhere, details concerning watermarking are known from Applicant's U.S. Pat. Nos. 6,122,403, 6,345,104, 6,424,725, 6,516,079, 6,590,996, 6,912,295, 6,988,202, 7,013,021, 7,076,082, 7,231,061, 7,978,875, 7,574,014, 7,013,021, 6,442,284, 20100150434, 20120078989, 20120129574, 20140052555, 20140304122, 20150278980, 20160063611, and 20160275639.

Linking from watermarks (or other identifiers) to corresponding online payoffs is detailed, e.g., in Digimarc's U.S. Pat. Nos. 6,947,571 and 7,206,820.

Arrangements for identifying regions within captured imagery that have higher probabilities of watermark detection are detailed in Applicant's U.S. Pat. Nos. 6,442,284, 6,516,079, 7,013,021 and 20150030201 (as well as in certain of the earlier-referenced documents). Another arrangement for setting camera exposure to capture imagery of watermarked objects is taught in U.S. Pat. No. 6,366,680. Publication 20160267620 teaches how watermarking can be used to ensure that components of multi-component packaging are assembled correctly.

This specification has discussed several different embodiments. It should be understood that the methods, elements and concepts detailed in connection with one embodiment can be combined with the methods, elements and concepts detailed in connection with other embodiments. While some such arrangements have been particularly described, some have not—due to the number of permutations and combinations. Applicant similarly recognizes and intends that the methods, elements and concepts of this specification can be combined, substituted and interchanged—not just among and between themselves, but also with those known from the cited prior art. Moreover, it will be recognized that the detailed technology can be included with other technologies—current and upcoming—to advantageous effect. Implementation of such combinations is straightforward to the artisan from the teachings provided in this disclosure.

While this disclosure has detailed particular ordering of acts and particular combinations of elements, it will be recognized that other contemplated methods may re-order acts (possibly omitting some and adding others), and other contemplated combinations may omit some elements and add others, etc.

Although disclosed as complete systems, sub-combinations of the detailed arrangements are also separately contemplated (e.g., omitting various of the features of a complete system).

While certain aspects of the technology have been described by reference to illustrative methods, it will be recognized that apparatuses configured to perform the acts of such methods are also contemplated as part of Applicant's inventive work. Likewise, other aspects have been described by reference to illustrative apparatus, and the methodology performed by such apparatus is likewise within the scope of the present technology. Still further, tangible computer readable media containing instructions for configuring a processor or other programmable system to perform such methods is also expressly contemplated.

To provide a comprehensive disclosure, while complying with the Patent Act's requirement of conciseness, Applicant incorporates-by-reference each of the documents referenced herein. (Such materials are incorporated in their entireties, even if cited above in connection with specific of their teachings.) These references disclose technologies and teachings that Applicant intends be incorporated into the arrangements detailed herein, and into which the technologies and teachings presently-detailed be incorporated.

In view of the wide variety of embodiments to which the principles and features discussed above can be applied, it should be apparent that the detailed embodiments are illustrative only, and should not be taken as limiting the scope of the invention. Rather, Applicant claims as the invention all such modifications as may come within the scope and spirit of the following claims and equivalents thereof.

The invention claimed is:

1. A camera configuration method comprising the acts:
capturing a first image of a subject with a camera, the camera employing a first combination of values for first and second imaging parameters, at least one of said first and second imaging parameters being selected from the group consisting of: exposure interval, camera gain, illumination intensity, and flash illumination interval;
computing a probability distribution measure, said probability distribution measure comprising a difference, or similarity, between a probability distribution of pixel values in the first image, and a second probability distribution;
capturing additional images of the subject with the camera, employing other combinations of values for said first and second imaging parameters, and, for each additional image, computing said probability distribution measure comprising a difference or similarity between a probability distribution of pixel values in the further image, and the second probability distribution;
identifying which combination of values for the first and second imaging parameters yields a most extreme value of said probability distribution measure; and
setting the camera to use said combination of values for the first and second imaging parameters in capturing subsequent images;
wherein said act of identifying a combination of values for the first and second imaging parameters yielding a most extreme value of said probability distribution measure has the practical effect of establishing an optimal set of imaging parameters to best allow machine detection of subtle features from imagery.

2. The method of claim 1 in which the probability distribution measure comprises an entropy metric, and the method includes identifying which combination of values for the first and second imaging parameters yielded a maximum value of said metric.

3. The method of claim 1 in which the probability distribution measure comprises a divergence metric, and the method includes identifying which combination of values for the first and second imaging parameters yielded a minimum value of said metric.

4. The method of claim 1 in which the second probability distribution is an idealized probability distribution.

5. The method of claim 1 that includes:
generating histogram data that counts pixels of different values in the first image;
determining an entropy or divergence metric from the histogram data;
for each of said additional images, generating histogram data, and determining an entropy or divergence metric from the histogram data;
identifying the combination of values for said first and second imaging parameters that yields the captured image having histogram data with the largest entropy metric, or with the smallest divergence metric.

6. The method of claim 1 that includes determining a Shannon entropy metric having the form:

$$H = \sum_{i=0}^{n} -(L_i/K) * \log2(L_i/K)$$

where n is the number of possible pixel values, K is the number of pixels in the image, and Li is the count of pixels in the image having value i.

7. The method of claim 1 in which both the first and second imaging parameters are selected from the list consisting of: exposure interval, lens aperture, camera gain, illumination intensity, and flash illumination interval.

8. The method of claim 1 in which one of said parameters comprises exposure interval, and the method includes initially determining said probability distribution measure with a first value for said exposure interval, and then decreasing the exposure interval for successive computations of said additional probability distribution measures, until a difference in said probability distribution measure between successive values of exposure interval changes sign.

9. The method of claim 1 in which said parameters comprise exposure interval and camera gain, and the method includes initially determining an entropy metric with a first value for said exposure interval and a first value for said camera gain, and thereafter alternately decreasing the exposure interval and camera gain for successive determinations of additional entropy metrics, until decreasing a first of said parameters yields a decline in entropy metric, and thereafter continuing to reduce the second of said parameters until decreasing the second parameter also yields a decline in entropy metric.

10. The method of claim 1 that includes filtering the captured images before computing said probability distribution measures, said filtering comprising, for each of plural pixels in each captured image, determining whether a value of said pixel is less than, equal to, or greater than, a value of each of eight neighboring pixels, and changing the value of said pixel in accordance with said eight determinations.

11. The method of claim 1 that includes computing said probability distribution measures for each of plural blocks in plural of said captured images, and for each block, identifying which combination of values for the first and second imaging parameters yielded the most extreme value of said probability distribution measure.

12. The method of claim 1 that further includes extracting information from one of said subsequent images, by optical character recognition, barcode decoding, image fingerprint recognition, recognition by a neural network, or watermark detection.

13. An inspection system for a production line that packages food or that applies labels to food containers, comprising:
a camera directed towards the production line to capture imagery of objects conveyed by the production line, the camera employing first and second imaging parameters, at least one of said first and second imaging parameters being selected from the group consisting of: exposure interval, camera gain, illumination intensity, and flash illumination interval; and
means for determining optimal values of said first and second imaging parameters, to best allow decoding of payload data from 2D indicia on said objects depicted in imagery captured by said camera, wherein said means includes:
software executing on a processor that causes the system to repeatedly collect image data from one or more objects, using different combinations of values for the first and second imaging parameters;
software executing on a processor that causes the system to determine, from the collected image data, for each different combination of values for the first and second imaging parameters, an entropy or divergence value; and
software executing on a processor that causes the system identify which of said different combinations of values for the first and second imaging parameters yields a largest entropy value or a smallest divergence value;
wherein the combination of values for the first and second imaging values thereby identified is determined to comprise said optimal values for said first and second imaging parameters.

14. The system of claim 13 that further includes means for decoding a 2D machine-readable symbology captured with said camera using said values of first and second imaging parameters determined to be optimal.

15. A method comprising the acts:
capturing plural image frames depicting a subject with a camera in an environment, the camera capturing each image frame with a particular combination of values for first and second imaging parameters, at least one of said first and second imaging parameters being selected from the group consisting of: exposure interval, camera gain, illumination intensity, and flash illumination interval, wherein different of said image frames are captured with different combinations of values for said first and second imaging parameters;
analyzing the captured image frames to identify which of said combinations of imaging parameter values is optimum for capture of imagery by said camera in said environment, by computing entropy or divergence metrics from the captured image frames, and identifying an extrema of said computed metrics; and
setting the camera to employ said identified combination of imaging parameter values in capturing an image of an object;
wherein the method has the practical effect of establishing an optimal set of imaging parameters for capturing images with said camera in said environment.

16. The method of claim 15 that further includes decoding a payload from a 2D data-carrying symbology depicted in imagery of said object captured by said camera using said identified combination of imaging parameter values.

17. The method of claim 15 in which the analyzing act comprises computing a Shannon entropy metric.

18. The method of claim 15 in which both the first and second imaging parameters are selected from the list consisting of: exposure interval, lens aperture, camera gain, illumination intensity, and flash illumination interval.

19. The method of claim 15 that includes:
identifying, within each of the plural captured image frames, several spatially-distributed blocks; and
computing entropy metrics for each of said spatially-distributed blocks;
wherein the method determines a first optimum combination of imaging parameter values for a first block within imagery captured by said camera, and determines a second optimum combination of imaging parameter values for a second block within imagery captured by said camera.

20. The method of claim 15 in which the subject is a gradient test pattern.

21. The method of claim 15 in which the subject is not a gradient test pattern.

22. The method of claim 21 in which the subject comprises packages on a production line that packages goods or that applied labels to packaging.

23. A non-transitory computer readable medium containing software instructions for configuring a computer to control an inspection system to perform the acts of claim 15.

24. The method of claim 1 in which the subject comprises a printed greyscale gradient target.

25. The method of claim 24 that further includes:
replacing the target with a printed package; and
capturing an image of the package with the camera, employing said identified combination of values for the first and second imaging parameters.

26. The method of claim 25 that includes decoding a machine-readably symbology from the captured image of said package.

27. The method of claim 1 in which the camera is a greyscale camera that produces pixels having values in the set {0, 1, 2, . . . 255}.

28. The method of claim 5 in which each of said histograms comprises 256 values, respectively corresponding to pixel values in said set {0, 1, 2, . . . 255}.

29. The method of claim 1 that includes filtering the captured images to reduce noise effects, before computing said probability distribution measures.

* * * * *

UNITED STATES PATENT AND TRADEMARK OFFICE
CERTIFICATE OF CORRECTION

Page 1 of 1

PATENT NO. : 10,593,007 B1
APPLICATION NO. : 15/816098
DATED : March 17, 2020
INVENTOR(S) : Scott M. Long and Christopher M. Haverkate It is certified that error appears in the above-identified patent and that said Letters Patent is hereby corrected as shown below:

On the Title Page

Column 1, item (63) Related U.S. Application Data, Line 2, change "June 18, 2016" to
-- June 8, 2016 --.

Signed and Sealed this
Eleventh Day of August, 2020

Andrei Iancu
*Director of the United States Patent and Trademark Office*